United States Patent
Webb et al.

(10) Patent No.: US 10,687,935 B2
(45) Date of Patent: Jun. 23, 2020

(54) METHODS OF MOLDING INTRAOCULAR LENSES

(71) Applicant: AcuFocus, Inc., Irvine, CA (US)

(72) Inventors: R. Kyle Webb, Carlsbad, CA (US); Nicholas Tarantino, Capistrano Beach, CA (US); Daniel David Siems, Aliso Viejo, CA (US)

(73) Assignee: AcuFocus, Inc., Irvine, CA (US)

( * ) Notice: Subject to any disclaimer, the term of this patent is extended or adjusted under 35 U.S.C. 154(b) by 64 days.

(21) Appl. No.: 15/765,611

(22) PCT Filed: Oct. 3, 2016

(86) PCT No.: PCT/US2016/055207
§ 371 (c)(1),
(2) Date: Apr. 3, 2018

(87) PCT Pub. No.: WO2017/062316
PCT Pub. Date: Apr. 13, 2017

(65) Prior Publication Data
US 2019/0076235 A1    Mar. 14, 2019

Related U.S. Application Data

(60) Provisional application No. 62/237,429, filed on Oct. 5, 2015.

(51) Int. Cl.
*A61F 2/14* (2006.01)
*A61F 2/16* (2006.01)
(Continued)

(52) U.S. Cl.
CPC .................. *A61F 2/15* (2015.04); *A61F 2/16* (2013.01); *B29D 11/00442* (2013.01); *B29D 11/023* (2013.01); *A61F 2002/1696* (2015.04)

(58) Field of Classification Search
CPC ....................................................... A61F 2/14
See application file for complete search history.

(56) References Cited

U.S. PATENT DOCUMENTS 2,350,421 A    6/1944 Schoder et al.
2,470,927 A    5/1949 Hale, Jr.
(Continued)

FOREIGN PATENT DOCUMENTS

AU    2004201751    5/2004
CN    1875895    12/2006
(Continued)

OTHER PUBLICATIONS

Internet Archive Wayback Machine; Aniridia Implants; downloaded from https://web.archive.org/web/20110824062840/http://www.morcher.com/nc/produkte/aniridiaimplants.html (Archived Aug. 24, 2011; printed on Feb. 5, 2015).
(Continued)

*Primary Examiner* — Matthew W Schall
(74) *Attorney, Agent, or Firm* — Knobbe, Martens, Olson & Bear, LLP

(57) ABSTRACT

Intraocular implants and methods of making intraocular implants are disclosed. The intraocular implant can include a mask adapted to increase depth of focus. The method of manufacturing the implant can include filling an annular mask-forming trough with an opaque mask material and adding an optically transmissive optic material over the opaque mask material.

16 Claims, 14 Drawing Sheets

(51) Int. Cl.
   *B29D 11/00* (2006.01)
   *B29D 11/02* (2006.01)

(56) References Cited

U.S. PATENT DOCUMENTS

| | | |
|---|---|---|
| 3,034,403 A | 5/1962 | Neefe |
| 3,270,099 A | 8/1966 | Camp |
| 3,458,870 A | 8/1969 | Stone |
| 3,578,850 A | 5/1971 | Grant |
| 3,776,230 A | 12/1973 | Neefe |
| 3,794,414 A | 2/1974 | Wesley |
| 3,877,502 A | 4/1975 | Hunckler |
| 3,996,627 A | 12/1976 | Deeg et al. |
| 4,010,496 A | 3/1977 | Neefe |
| 4,104,338 A | 8/1978 | Guerrieri |
| 4,116,439 A | 9/1978 | Chavarria et al. |
| 4,210,391 A | 7/1980 | Cohen |
| 4,298,996 A | 11/1981 | Barnet |
| 4,340,283 A | 7/1982 | Cohen |
| 4,402,579 A | 9/1983 | Poler |
| 4,423,728 A | 1/1984 | Lieberman |
| 4,435,050 A | 3/1984 | Poler |
| 4,450,593 A | 5/1984 | Poler |
| 4,505,855 A | 3/1985 | Bruns et al. |
| 4,512,039 A | 4/1985 | Lieberman |
| 4,563,565 A | 1/1986 | Kampfer et al. |
| 4,575,373 A | 3/1986 | Johnson |
| 4,596,578 A | 6/1986 | Kelman |
| 4,607,617 A | 8/1986 | Choyce |
| 4,624,669 A | 11/1986 | Grendahl |
| 4,639,105 A | 1/1987 | Neefe |
| 4,646,720 A | 3/1987 | Peyman et al. |
| 4,655,774 A | 4/1987 | Choyce |
| 4,665,913 A | 5/1987 | Esperance, Jr. |
| 4,669,466 A | 6/1987 | L'Esperance |
| 4,669,834 A | 6/1987 | Richter |
| 4,676,790 A | 6/1987 | Kern |
| 4,676,791 A | 6/1987 | LeMaster et al. |
| 4,678,422 A | 7/1987 | York |
| 4,701,038 A | 10/1987 | Neefe |
| 4,715,858 A | 12/1987 | Lindstrom |
| 4,767,647 A | 8/1988 | Bree |
| 4,795,462 A | 1/1989 | Grendahl |
| 4,798,608 A | 1/1989 | Grendahl |
| 4,799,784 A | 1/1989 | Safir |
| 4,799,931 A | 1/1989 | Lindstrom |
| 4,807,623 A | 2/1989 | Lieberman |
| 4,813,955 A | 3/1989 | Achatz et al. |
| 4,815,690 A | 3/1989 | Shepherd |
| 4,817,789 A | 4/1989 | Paul |
| 4,830,855 A | 5/1989 | Stewart |
| 4,842,599 A | 6/1989 | Bronstein |
| 4,842,782 A | 6/1989 | Portney |
| 4,851,003 A | 7/1989 | Lindstrom |
| 4,863,466 A | 9/1989 | Schlegel |
| 4,881,860 A | 11/1989 | Kanazawa |
| 4,903,695 A | 2/1990 | Warner et al. |
| 4,907,586 A | 3/1990 | Bille et al. |
| 4,928,815 A | 5/1990 | Paul |
| 4,955,904 A | 9/1990 | Atebara et al. |
| 4,976,732 A | 12/1990 | Vorosmarthy |
| 4,994,080 A | 2/1991 | Shepard |
| 5,013,319 A | 5/1991 | Davis |
| 5,030,230 A | 7/1991 | White |
| 5,034,166 A | 7/1991 | Rawlings et al. |
| 5,041,133 A | 8/1991 | Sayano et al. |
| 5,055,602 A | 10/1991 | Melpolder |
| 5,087,015 A | 2/1992 | Galley |
| 5,090,955 A | 2/1992 | Simon |
| 5,092,880 A | 3/1992 | Ohmi |
| 5,094,521 A | 3/1992 | Jolson et al. |
| 5,098,443 A | 3/1992 | Parel et al. |
| 5,108,427 A | 4/1992 | Majercik et al. |
| 5,112,328 A | 5/1992 | Taboada et al. |
| 5,120,120 A | 6/1992 | Cohen |
| 5,120,121 A | 6/1992 | Rawlings et al. |
| 5,137,441 A | 8/1992 | Fogarty |
| 5,147,395 A | 9/1992 | Willis |
| 5,171,318 A | 12/1992 | Gibson et al. |
| 5,185,107 A | 2/1993 | Blake |
| 5,188,494 A | 2/1993 | Hatin |
| 5,192,316 A | 3/1993 | Ting |
| 5,196,026 A | 3/1993 | Barrett et al. |
| 5,213,749 A | 5/1993 | Huss et al. |
| 5,260,727 A | 11/1993 | Oksman et al. |
| 5,266,241 A | 11/1993 | Parekh |
| 5,269,795 A | 12/1993 | Arnott |
| 5,269,812 A | 12/1993 | White |
| 5,274,404 A | 12/1993 | Michael |
| 5,288,436 A | 2/1994 | Liu et al. |
| 5,290,892 A | 3/1994 | Namdaran et al. |
| 5,292,514 A | 3/1994 | Capecchi et al. |
| 5,300,116 A | 4/1994 | Chirila et al. |
| 5,312,330 A | 5/1994 | Klopotek |
| 5,314,439 A | 5/1994 | Sugita |
| 5,314,961 A | 5/1994 | Anton et al. |
| 5,332,802 A | 7/1994 | Kelman et al. |
| 5,336,261 A | 8/1994 | Barrett et al. |
| 5,354,331 A | 10/1994 | Schachar et al. |
| 5,358,520 A | 10/1994 | Patel |
| 5,372,580 A | 12/1994 | Simon et al. |
| 5,391,201 A | 2/1995 | Barrett et al. |
| 5,441,511 A | 8/1995 | Hanna |
| 5,474,548 A | 12/1995 | Knopp et al. |
| 5,507,740 A | 4/1996 | O'Donnell, Jr. |
| 5,507,806 A | 4/1996 | Blake |
| 5,547,468 A | 4/1996 | Simon et al. |
| D375,245 S | 11/1996 | Irving |
| 5,578,080 A | 11/1996 | McDonald |
| 5,603,774 A | 2/1997 | LeBoeuf et al. |
| 5,607,437 A | 3/1997 | Simon et al. |
| 5,624,456 A | 4/1997 | Hellenkamp |
| 5,627,613 A | 5/1997 | Kaneko |
| 5,628,794 A | 5/1997 | Lindstrom |
| 5,628,795 A | 5/1997 | Langerman |
| 5,647,865 A | 7/1997 | Swinger |
| 5,652,638 A | 7/1997 | Roffman et al. |
| 5,653,752 A | 8/1997 | Silvestrini et al. |
| 5,662,706 A | 9/1997 | Legerton et al. |
| 5,674,284 A | 10/1997 | Chang et al. |
| 5,693,268 A | 12/1997 | Widman et al. |
| 5,697,923 A | 12/1997 | Poler |
| 5,702,440 A | 12/1997 | Portney |
| 5,708,049 A | 1/1998 | Katagiri et al. |
| 5,713,957 A | 2/1998 | Steele et al. |
| 5,722,971 A | 3/1998 | Peyman |
| 5,725,575 A | 3/1998 | O'Donnell, Jr. |
| 5,746,558 A | 5/1998 | Nygren et al. |
| 5,752,967 A | 5/1998 | Kritzinger et al. |
| 5,757,458 A | 5/1998 | Miller et al. |
| 5,769,889 A | 6/1998 | Kelman |
| 5,774,202 A | 6/1998 | Abraham et al. |
| 5,786,883 A | 7/1998 | Miller et al. |
| 5,824,086 A | 10/1998 | Silvestrini |
| 5,837,156 A | 11/1998 | Cumming |
| 5,843,105 A | 12/1998 | Mathis et al. |
| 5,864,128 A | 1/1999 | Plesko |
| 5,870,167 A | 2/1999 | Knopp et al. |
| 5,895,610 A | 4/1999 | Chang et al. |
| 5,905,561 A | 5/1999 | Lee et al. |
| 5,910,537 A | 6/1999 | Feingold et al. |
| 5,913,898 A | 6/1999 | Feingold et al. |
| 5,919,185 A | 7/1999 | Peyman |
| 5,925,294 A | 7/1999 | Shibuya |
| 5,964,748 A | 10/1999 | Peyman |
| 5,964,776 A | 10/1999 | Peyman |
| 5,965,330 A | 10/1999 | Evans et al. |
| 5,980,040 A | 11/1999 | Xu et al. |
| 6,017,121 A | 1/2000 | Chateau et al. |
| 6,063,073 A | 5/2000 | Peyman |
| 6,090,141 A | 7/2000 | Lindstrom |
| 6,102,946 A | 8/2000 | Nigam |
| 6,106,553 A | 8/2000 | Feingold et al. |
| 6,110,166 A | 8/2000 | Juhasz et al. |

(56) References Cited

U.S. PATENT DOCUMENTS

| | | |
|---|---|---|
| 6,138,307 A | 10/2000 | McDonald |
| 6,152,959 A | 11/2000 | Portney |
| 6,164,777 A | 12/2000 | Li et al. |
| 6,171,336 B1 | 1/2001 | Sawusch |
| 6,178,593 B1 | 1/2001 | Carlson |
| 6,197,019 B1 | 3/2001 | Peyman |
| 6,201,036 B1 | 3/2001 | Fedorov et al. |
| 6,203,538 B1 | 3/2001 | Peyman |
| 6,210,401 B1 | 4/2001 | Lai |
| 6,217,571 B1 | 4/2001 | Peyman |
| 6,217,596 B1 | 4/2001 | Farah |
| 6,221,067 B1 | 4/2001 | Peyman |
| 6,228,113 B1 | 5/2001 | Kaufman |
| 6,228,114 B1 | 5/2001 | Lee |
| 6,228,115 B1 | 5/2001 | Hoffmann et al. |
| 6,264,648 B1 | 7/2001 | Peyman |
| 6,277,146 B1 | 8/2001 | Peyman et al. |
| 6,280,470 B1 | 8/2001 | Peyman |
| 6,280,471 B1 | 8/2001 | Peyman et al. |
| 6,302,877 B1 | 10/2001 | Ruiz |
| 6,304,390 B1 | 10/2001 | Takanashi |
| 6,308,590 B1 | 10/2001 | Berto |
| 6,335,190 B1 | 1/2002 | Zhou et al. |
| 6,361,560 B1 | 3/2002 | Nigam |
| 6,376,153 B2 | 4/2002 | Uchikawa et al. |
| 6,387,379 B1 | 5/2002 | Goldberg et al. |
| 6,391,230 B1 | 5/2002 | Sarbadhikari |
| 6,416,179 B1 | 7/2002 | Lieberman et al. |
| 6,423,093 B1 | 7/2002 | Hicks et al. |
| 6,432,246 B1 | 8/2002 | Blake |
| 6,436,092 B1 | 8/2002 | Peyman |
| 6,458,141 B1 | 10/2002 | Peyman |
| 6,461,384 B1 | 10/2002 | Hoffmann et al. |
| 6,469,844 B1 | 10/2002 | Iwase et al. |
| 6,480,346 B2 | 11/2002 | Funakoshi |
| 6,491,637 B2 | 12/2002 | Foster et al. |
| 6,497,700 B1 | 12/2002 | LaHaye |
| 6,515,006 B2 | 2/2003 | Horn |
| 6,533,416 B1 | 3/2003 | Fermigier et al. |
| 6,551,307 B2 | 4/2003 | Peyman |
| 6,554,424 B1 | 4/2003 | Miller et al. |
| 6,554,860 B2 | 4/2003 | Hoffmann et al. |
| 6,555,103 B2 | 4/2003 | Leukel et al. |
| 6,575,573 B2 | 6/2003 | Lai et al. |
| 6,581,993 B2 | 6/2003 | Nigam |
| 6,588,902 B2 | 7/2003 | Isogai |
| 6,589,280 B1 | 7/2003 | Koziol |
| 6,607,527 B1 | 8/2003 | Ruiz et al. |
| 6,613,088 B1 | 9/2003 | Babizhayev |
| 6,638,304 B2 | 10/2003 | Azar |
| 6,649,722 B2 | 11/2003 | Rosenzweig et al. |
| 6,655,804 B2 | 12/2003 | Streibig |
| 6,692,126 B1 | 2/2004 | Xie et al. |
| 6,702,807 B2 | 3/2004 | Peyman |
| 6,726,322 B2 | 4/2004 | Andino et al. |
| 6,740,116 B2 | 5/2004 | Morcher |
| 6,755,858 B1 | 6/2004 | White |
| 6,786,926 B2 | 9/2004 | Peyman |
| 6,811,256 B1 | 11/2004 | Becherer et al. |
| 6,855,163 B2 | 2/2005 | Peyman |
| 6,874,886 B2 | 4/2005 | Miller et al. |
| 6,899,424 B2 | 5/2005 | Miller et al. |
| 6,949,093 B1 | 9/2005 | Peyman |
| 6,951,556 B2 | 10/2005 | Epstein |
| 6,966,648 B2 | 11/2005 | Miller et al. |
| 6,989,008 B2 | 1/2006 | Peyman |
| 6,997,428 B1 | 2/2006 | Andino et al. |
| 7,001,374 B2 | 2/2006 | Peyman |
| 7,008,447 B2 | 3/2006 | Koziol |
| 7,025,455 B2 | 4/2006 | Roffman |
| 7,061,693 B2 | 6/2006 | Zalevsky |
| 7,099,057 B2 | 8/2006 | Parker et al. |
| 7,276,080 B2 | 10/2007 | Murakami et al. |
| 7,287,852 B2 | 10/2007 | Fiala |
| 7,364,674 B1 | 4/2008 | Hoover |
| 7,399,811 B2 | 7/2008 | Mentak et al. |
| 7,404,637 B2 | 7/2008 | Miller et al. |
| 7,404,638 B2 | 7/2008 | Miller et al. |
| 7,446,157 B2 | 11/2008 | Mentak et al. |
| 7,455,404 B2 | 11/2008 | Bandhauer et al. |
| 7,455,691 B2 | 11/2008 | Feingold et al. |
| 7,462,193 B2 | 12/2008 | Nagamoto |
| 7,477,452 B2 | 1/2009 | Tsuruma |
| 7,491,350 B2 | 2/2009 | Silvestrini |
| 7,497,866 B2 | 3/2009 | Perez |
| 7,628,810 B2 | 12/2009 | Christie et al. |
| 7,641,337 B2 | 1/2010 | Altmann |
| 7,645,299 B2 | 1/2010 | Koziol |
| 7,745,555 B2 | 6/2010 | Mentak et al. |
| 7,780,290 B2 | 8/2010 | Zhao |
| 7,842,367 B2 | 11/2010 | Mentak |
| 7,976,577 B2 | 7/2011 | Silvestrini |
| D645,337 S | 9/2011 | Hsu et al. |
| 8,043,371 B2 | 10/2011 | Paul et al. |
| 8,048,972 B2 | 11/2011 | Mentak et al. |
| 8,079,706 B2 | 12/2011 | Silvestrini et al. |
| D656,526 S | 3/2012 | Christie et al. |
| 8,157,374 B2 | 4/2012 | Bandhauer et al. |
| 8,241,354 B2 | 8/2012 | Hong et al. |
| 8,287,592 B2 | 10/2012 | Silvestrini |
| 8,343,215 B2 | 1/2013 | Miller et al. |
| D681,086 S | 4/2013 | Christie et al. |
| 8,420,753 B2 | 4/2013 | Mentak et al. |
| 8,439,498 B2 | 5/2013 | Zhao et al. |
| 8,460,374 B2 | 6/2013 | Christie et al. |
| 8,562,131 B2 | 10/2013 | Zhao |
| 8,604,098 B2 | 12/2013 | Boydston et al. |
| 8,740,978 B2 | 6/2014 | Weeber et al. |
| 8,747,466 B2 | 6/2014 | Weeber et al. |
| 8,752,958 B2 | 6/2014 | Miller et al. |
| 8,633,292 B2 | 7/2014 | Hu et al. |
| 8,858,624 B2 | 10/2014 | Christie et al. |
| 8,864,824 B2 | 10/2014 | Silvestrini et al. |
| 8,955,968 B2 | 2/2015 | Zalevsky et al. |
| 9,005,281 B2 | 4/2015 | Christie et al. |
| 9,138,142 B2 | 9/2015 | Christie et al. |
| 9,204,962 B2 | 12/2015 | Silvestrini |
| 9,427,311 B2 | 8/2016 | Christie et al. |
| 9,427,922 B2 | 8/2016 | Reboul et al. |
| 9,492,272 B2 | 11/2016 | Christie et al. |
| 9,545,303 B2 | 1/2017 | Vilupuru et al. |
| 9,573,328 B2 | 2/2017 | Reboul et al. |
| 9,603,704 B2 | 3/2017 | Silvestrini |
| 9,744,077 B2 | 8/2017 | Zicker et al. |
| 9,757,227 B2 | 9/2017 | Kushlin et al. |
| 9,844,919 B2 | 12/2017 | Reboul et al. |
| 9,848,979 B2 | 12/2017 | Vilupuru et al. |
| 9,943,403 B2 | 4/2018 | Webb et al. |
| 9,987,127 B2 | 6/2018 | Bogaert et al. |
| 10,183,453 B2 | 1/2019 | Reboul et al. |
| 10,342,656 B2 | 7/2019 | Vilupuru et al. |
| 10,350,058 B2 | 7/2019 | Silvestrini |
| 10,426,600 B2 | 10/2019 | Coleman et al. |
| 10,449,036 B2 | 10/2019 | Christie et al. |
| 2001/0027314 A1 | 10/2001 | Peyman |
| 2001/0034516 A1 | 10/2001 | Peyman |
| 2001/0050750 A1 | 12/2001 | Breger |
| 2002/0010510 A1 | 1/2002 | Silverstrini |
| 2002/0082288 A1 | 6/2002 | Horn |
| 2002/0120329 A1 | 8/2002 | Lang et al. |
| 2002/0128710 A1 | 9/2002 | Eggleston |
| 2002/0167640 A1 | 11/2002 | Francis et al. |
| 2002/0196409 A1 | 12/2002 | Jani |
| 2003/0014042 A1 | 1/2003 | Juhasz et al. |
| 2003/0060880 A1 | 3/2003 | Feingold |
| 2003/0105521 A1 | 6/2003 | Perez |
| 2003/0135272 A1 | 7/2003 | Brady et al. |
| 2003/0149480 A1 | 8/2003 | Shadduck |
| 2003/0204258 A1 | 10/2003 | Graham et al. |
| 2003/0216763 A1 | 11/2003 | Patel |
| 2004/0019379 A1 | 1/2004 | Glick et al. |
| 2004/0056371 A1 | 3/2004 | Liao et al. |
| 2004/0068317 A1 | 4/2004 | Knight |
| 2004/0106929 A1 | 6/2004 | Masket |

(56) References Cited

U.S. PATENT DOCUMENTS

| | | |
|---|---|---|
| 2004/0140578 A1 | 7/2004 | Kelly et al. |
| 2005/0027355 A1 | 2/2005 | Murakami et al. |
| 2005/0046794 A1 | 3/2005 | Silvestrini et al. |
| 2005/0056954 A1 | 3/2005 | Devlin |
| 2005/0090895 A1 | 4/2005 | Peyman |
| 2005/0124983 A1 | 6/2005 | Frey et al. |
| 2005/0134793 A1 | 6/2005 | Roffman |
| 2005/0137703 A1 | 6/2005 | Chen |
| 2005/0143751 A1 | 6/2005 | Makker et al. |
| 2005/0182488 A1 | 8/2005 | Peyman |
| 2005/0187621 A1 | 8/2005 | Brady |
| 2005/0288784 A1 | 12/2005 | Peyman |
| 2006/0064077 A1 | 3/2006 | Peyman |
| 2006/0079959 A1 | 4/2006 | Christie et al. |
| 2006/0113054 A1 | 6/2006 | Silvestrini |
| 2006/0184243 A1 | 8/2006 | Yilmaz |
| 2006/0232665 A1 | 10/2006 | Schowengerdt et al. |
| 2006/0235428 A1 | 10/2006 | Silvestrini |
| 2006/0235514 A1 | 10/2006 | Silvestrini |
| 2006/0241751 A1 | 10/2006 | Marmo et al. |
| 2006/0247659 A1 | 11/2006 | Moeller et al. |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |
| 2007/0032866 A1 | 2/2007 | Portney |
| 2007/0091472 A1 | 4/2007 | Alkemper et al. |
| 2007/0092592 A1 | 4/2007 | Chiang |
| 2007/0129797 A1 | 6/2007 | Lang et al. |
| 2007/0225691 A1 | 9/2007 | Silvestrini et al. |
| 2008/0033546 A1 | 2/2008 | Liang |
| 2008/0077238 A1 | 3/2008 | Deacon et al. |
| 2008/0100921 A1 | 5/2008 | Nishikawa |
| 2008/0151183 A1 | 6/2008 | Altmann |
| 2008/0208335 A1 | 8/2008 | Blum et al. |
| 2008/0212030 A1 | 9/2008 | Bentley et al. |
| 2008/0220214 A1 | 9/2008 | Uozu et al. |
| 2008/0221674 A1 | 9/2008 | Blum et al. |
| 2008/0255663 A1 | 10/2008 | Akpek et al. |
| 2008/0269884 A1 | 10/2008 | Vannoy |
| 2008/0306587 A1 | 12/2008 | Your |
| 2009/0012505 A1 | 1/2009 | Chernyak |
| 2009/0021692 A1 | 1/2009 | Miller et al. |
| 2009/0287306 A1 | 1/2009 | Smith et al. |
| 2009/0036880 A1 | 2/2009 | Bischoff et al. |
| 2009/0048608 A1 | 2/2009 | Boukhny et al. |
| 2009/0059168 A1 | 3/2009 | Miller et al. |
| 2009/0069817 A1 | 3/2009 | Peyman |
| 2009/0164008 A1 | 6/2009 | Hong et al. |
| 2009/0171458 A1 | 7/2009 | Kellan et al. |
| 2009/0187242 A1 | 7/2009 | Weeber et al. |
| 2009/0204207 A1 | 8/2009 | Blum et al. |
| 2009/0213326 A1 | 8/2009 | Zhao |
| 2009/0222086 A1 | 9/2009 | Lui et al. |
| 2009/0234448 A1 | 9/2009 | Weeber et al. |
| 2009/0279048 A1 | 11/2009 | Hong et al. |
| 2009/0306773 A1 | 12/2009 | Silversrini et al. |
| 2010/0016961 A1 | 1/2010 | Hong et al. |
| 2010/0016965 A1 | 1/2010 | Hong et al. |
| 2010/0082100 A1 | 4/2010 | Mikawa |
| 2010/0127412 A1 | 5/2010 | Lake |
| 2010/0149618 A1 | 6/2010 | Sprague |
| 2010/0208199 A1 | 8/2010 | Levis et al. |
| 2010/0225014 A1 | 9/2010 | Bille |
| 2010/0312336 A1 | 12/2010 | Hong et al. |
| 2011/0037184 A1 | 2/2011 | Shoji et al. |
| 2011/0051080 A1 | 3/2011 | Bandhauer et al. |
| 2011/0125261 A1 | 5/2011 | Portney |
| 2011/0166652 A1 | 7/2011 | Bogaert et al. |
| 2011/0172675 A1 | 7/2011 | Danta et al. |
| 2011/0245919 A1 | 10/2011 | Pettit |
| 2011/0251685 A1 | 10/2011 | Chu |
| 2011/0292340 A1 | 12/2011 | Shimizu et al. |
| 2012/0203239 A1 | 8/2012 | Vukich et al. |
| 2012/0245683 A1 | 9/2012 | Christie et al. |
| 2012/0309761 A1 | 12/2012 | Chow et al. |
| 2012/0310338 A1 | 12/2012 | Christie et al. |
| 2013/0053953 A1 | 2/2013 | Silvestrini |
| 2013/0131795 A1 | 5/2013 | Miller et al. |
| 2013/0147072 A1 | 6/2013 | Bothe et al. |
| 2013/0238091 A1 | 9/2013 | Danta et al. |
| 2013/0268071 A1* | 10/2013 | Vilupuru ............... A61B 3/102 623/6.17 |
| 2013/0289543 A1 | 10/2013 | Mordaunt |
| 2014/0121767 A1 | 5/2014 | Simpson |
| 2014/0131905 A1 | 5/2014 | Webb |
| 2014/0200666 A1 | 7/2014 | Phillips |
| 2014/0336625 A1 | 11/2014 | Fernandez |
| 2014/0343541 A1 | 11/2014 | Scott et al. |
| 2014/0379078 A1 | 12/2014 | Trindade |
| 2015/0025627 A1 | 1/2015 | Christie et al. |
| 2015/0046094 A1 | 2/2015 | Chaudhary et al. |
| 2015/0073549 A1 | 3/2015 | Webb et al. |
| 2015/0177422 A1 | 6/2015 | Liu et al. |
| 2015/0183173 A1 | 7/2015 | Linhardt et al. |
| 2015/0250583 A1 | 9/2015 | Rosen et al. |
| 2015/0366658 A1 | 12/2015 | Christie et al. |
| 2016/0100938 A1 | 4/2016 | Bogaert et al. |
| 2016/0135947 A1 | 5/2016 | Webb et al. |
| 2016/0297107 A1 | 10/2016 | Shim et al. |
| 2017/0049560 A1 | 2/2017 | Cherne |
| 2017/0143477 A1 | 5/2017 | Christie et al. |
| 2017/0156850 A1 | 6/2017 | Silvestrini et al. |
| 2018/0125639 A1 | 5/2018 | Vilupuru et al. |
| 2018/0133990 A1 | 5/2018 | Reboul et al. |
| 2018/0296322 A1 | 10/2018 | Webb et al. |
| 2018/0338826 A1 | 11/2018 | Link et al. |
| 2019/0076241 A1 | 3/2019 | Alarcon Heredia et al. |
| 2019/0269499 A1 | 9/2019 | Ellis |

FOREIGN PATENT DOCUMENTS

| | | |
|---|---|---|
| CN | 100368846 | 2/2008 |
| CN | 101322663 | 12/2008 |
| CN | 101341426 B | 7/2012 |
| CN | 203647535 | 6/2014 |
| DE | 2727410 A1 | 12/1978 |
| DE | 4134320 | 4/1992 |
| EP | 0165652 | 12/1985 |
| EP | 0443094 | 8/1991 |
| EP | 1173790 | 1/2002 |
| EP | 1674049 | 6/2006 |
| EP | 1548489 B1 | 8/2006 |
| EP | 2111822 | 10/2009 |
| EP | 2319457 | 5/2011 |
| EP | 2243052 B1 | 9/2011 |
| EP | 2365379 | 9/2011 |
| EP | 2455799 | 5/2012 |
| EP | 2823789 | 1/2015 |
| EP | 2364457 B1 | 8/2015 |
| EP | 2993514 A1 | 3/2016 |
| EP | 2349150 B1 | 7/2016 |
| FR | 2620687 | 3/1989 |
| FR | 2649605 | 1/1991 |
| GB | 1276003 | 6/1972 |
| GB | 2507465 | 5/2014 |
| JP | 62-167343 | 7/1987 |
| JP | 64-002644 | 1/1989 |
| JP | H02-7954 | 1/1990 |
| JP | 04-158859 | 6/1992 |
| JP | 06-509731 | 3/1993 |

(56) References Cited

FOREIGN PATENT DOCUMENTS

| | | |
|---|---|---|
| JP | H05-65340 | 9/1993 |
| JP | 06-502782 | 3/1994 |
| JP | H07-067896 | 3/1995 |
| JP | 07-265340 | 10/1995 |
| JP | 08-103457 A | 4/1996 |
| JP | H09-502542 | 3/1997 |
| JP | 11-503657 | 8/1997 |
| JP | 07-178125 | 7/1998 |
| JP | 2000-047145 | 2/2000 |
| JP | 2002-537895 | 11/2002 |
| JP | 2003-502109 | 1/2003 |
| JP | 2004-510199 | 4/2004 |
| JP | 2004-538034 | 12/2004 |
| JP | 2005-533576 | 11/2005 |
| JP | 2007-516794 | 6/2007 |
| JP | 2007-523720 | 8/2007 |
| JP | 2008-506710 | 3/2008 |
| JP | S59-54527 | 5/2008 |
| KR | 10-0335722 | 5/2002 |
| RU | 2138837 | 9/1999 |
| RU | 2456968 | 7/2012 |
| RU | 2457812 | 8/2012 |
| RU | 2459598 | 8/2012 |
| RU | 2493801 | 9/2013 |
| RU | 134049 | 11/2013 |
| RU | 134784 | 11/2013 |
| RU | 2500368 | 12/2013 |
| RU | 2511081 | 4/2014 |
| RU | 2517488 | 5/2014 |
| SU | 1380743 A1 | 3/1988 |
| TW | 201103518 | 2/2011 |
| WO | WO 87/05797 | 10/1987 |
| WO | WO 95/03747 | 2/1995 |
| WO | WO 95/08135 | 3/1995 |
| WO | WO 96/35397 | 11/1996 |
| WO | WO 98/48715 | 11/1998 |
| WO | WO 00/025704 | 5/2000 |
| WO | WO 00/038594 | 7/2000 |
| WO | WO 00/51682 | 9/2000 |
| WO | WO 00/52516 | 9/2000 |
| WO | WO 00/70388 | 11/2000 |
| WO | WO 2001/010641 | 2/2001 |
| WO | WO 01/15779 | 3/2001 |
| WO | WO 01/17460 | 3/2001 |
| WO | WO 01/19364 | 3/2001 |
| WO | WO 01/082815 | 11/2001 |
| WO | WO 02/076320 | 10/2002 |
| WO | WO 02/102241 | 12/2002 |
| WO | WO 03/020177 | 3/2003 |
| WO | WO 03/022168 | 3/2003 |
| WO | WO 03/061518 | 7/2003 |
| WO | WO 2004/014969 | 2/2004 |
| WO | WO 2004/034917 | 4/2004 |
| WO | WO 2004/105588 | 12/2004 |
| WO | WO 2004/113959 | 12/2004 |
| WO | WO 2005/082265 | 9/2005 |
| WO | WO 2006/020638 | 2/2006 |
| WO | WO 2006/047534 | 5/2006 |
| WO | WO 2006/060380 | 6/2006 |
| WO | WO 2006/069012 | 6/2006 |
| WO | WO 2006/113377 | 10/2006 |
| WO | WO 2006/113411 | 10/2006 |
| WO | WO 2006/113563 | 10/2006 |
| WO | WO 2006/113564 | 10/2006 |
| WO | WO 2007/057734 | 10/2007 |
| WO | WO 2007/133384 | 11/2007 |
| WO | WO 2007/142981 | 12/2007 |
| WO | WO 2008/036671 | 3/2008 |
| WO | WO 2008/102096 | 8/2008 |
| WO | WO 2009/050511 | 4/2009 |
| WO | WO 2009/122409 | 10/2009 |
| WO | WO 2009/140080 | 11/2009 |
| WO | WO 2009/149060 | 12/2009 |
| WO | WO 2010/002215 | 1/2010 |
| WO | WO 2010/059214 | 5/2010 |
| WO | WO 2010/118469 | 10/2010 |
| WO | WO 2011/020074 | 2/2011 |
| WO | WO 2011/020078 | 2/2011 |
| WO | WO 2011/047076 | 4/2011 |
| WO | WO 2011/069059 | 6/2011 |
| WO | WO 2011/088107 | 7/2011 |
| WO | WO 2012/170066 | 12/2012 |
| WO | WO 2011/030509 | 2/2013 |
| WO | WO 2013/019871 | 2/2013 |
| WO | WO 2013/082545 | 6/2013 |
| WO | WO 2013/101793 | 7/2013 |
| WO | WO 2013/112589 | 8/2013 |
| WO | WO 2013/123265 | 8/2013 |
| WO | WO 2014/054946 | 4/2014 |
| WO | WO 2014/074610 | 5/2014 |
| WO | WO 2014/158653 | 10/2014 |
| WO | WO 2014/164056 | 10/2014 |
| WO | WO 2014/195059 | 12/2014 |
| WO | WO 2015/021323 | 2/2015 |
| WO | WO 2015/069927 | 5/2015 |
| WO | WO 2015/073718 | 5/2015 |
| WO | WO 2015/078271 | 6/2015 |
| WO | WO 2015/086611 | 6/2015 |
| WO | WO 2016/081493 | 5/2016 |
| WO | WO 2015/108156 | 3/2017 |
| WO | WO 2017/062316 | 4/2017 |
| WO | WO 2017/091520 | 6/2017 |
| WO | WO 2019/010178 | 1/2019 |

OTHER PUBLICATIONS

Guyton A.C., Textbook of Medical Physiology, 7th Edition, W.B. Saunders Company, Jan. 1986: Chapter 58, pp. 700-710.

International Search Report and Written Opinion for PCT/US2016/055207 dated Jan. 18, 2017 in 15 pages.

Lu Xuequan, et al. "Radiation preparation and thermo-response swelling of interpenetrating polymer network hydrogel composed of PNIPAAm and PMMA", Radiation Physics and Chemistry, vol. 57, Mar. 2000, pp. 477-480, XP002473596.

Patel, C.K., et al. "Imaging the macula through a black occlusive intraocular lens". Arch. Ophthalmol. Oct. 2010; 128(10):1374-1376.

Yusuf, et al., "Inability to perform posterior segment monitoring by scanning laser ophthalmoscopy or optical coherence tomography with some occlusive intraocular lenses in clinical use", J. Cataract Refract. Surg., Mar. 2012, 38: 513-518.

Yusuf, et al., "Occlusive IOLs for Intractable Diplopia Demonstrate a Novel Near-Infrared Window of Transmission for SLO/OCT Imaging and Clinical Assessment". Investigative Ophthalmology & Visual Science, May 2011, 52(6): 3737-3743.

\* cited by examiner

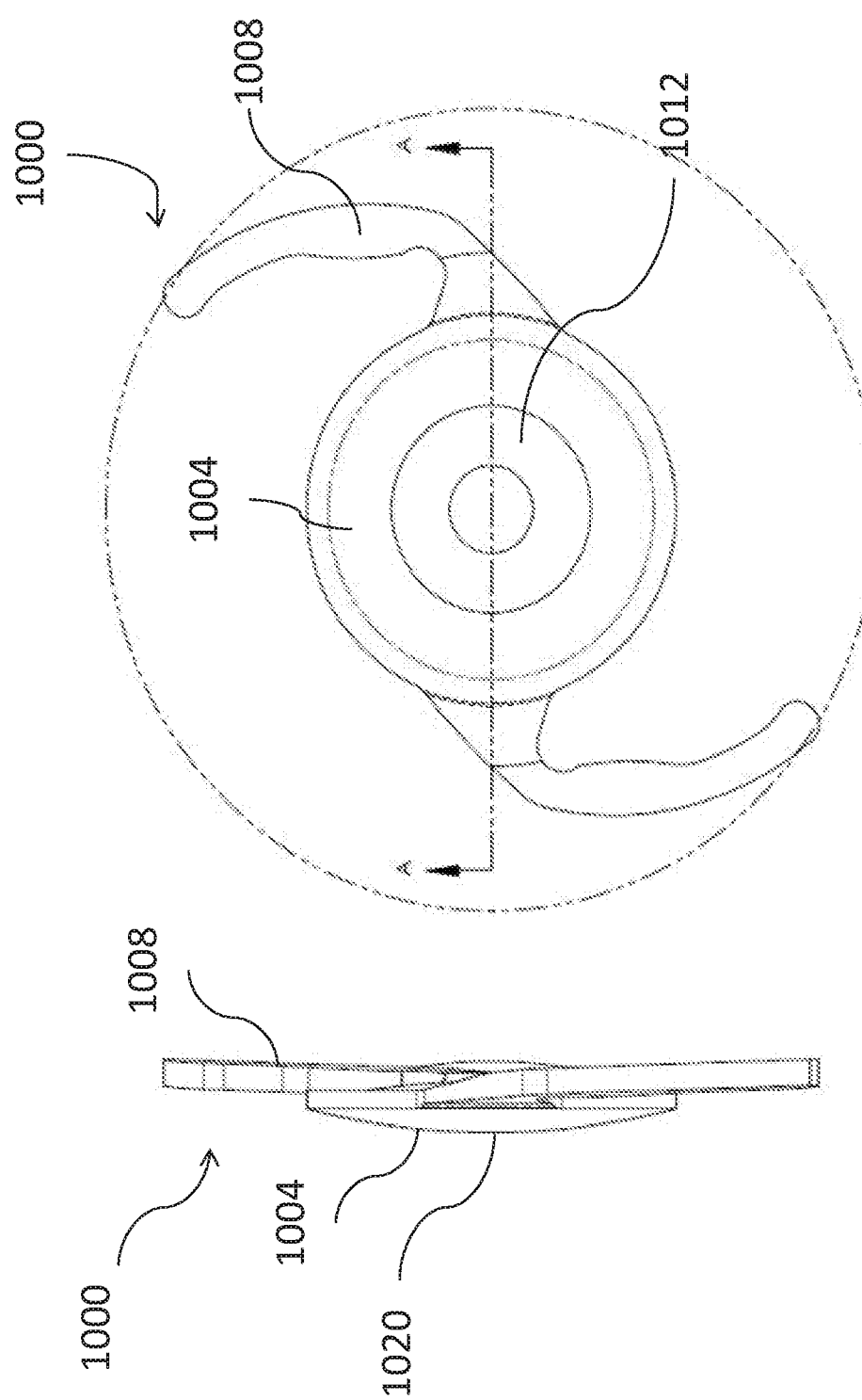

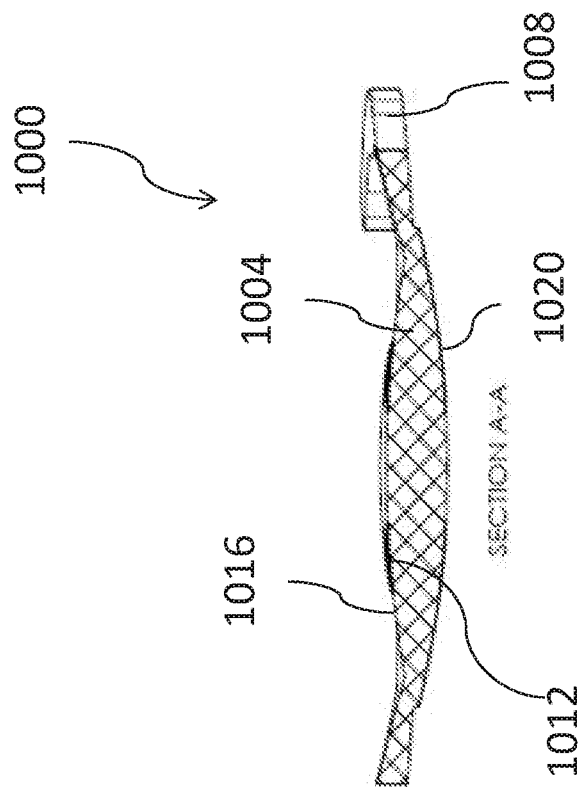
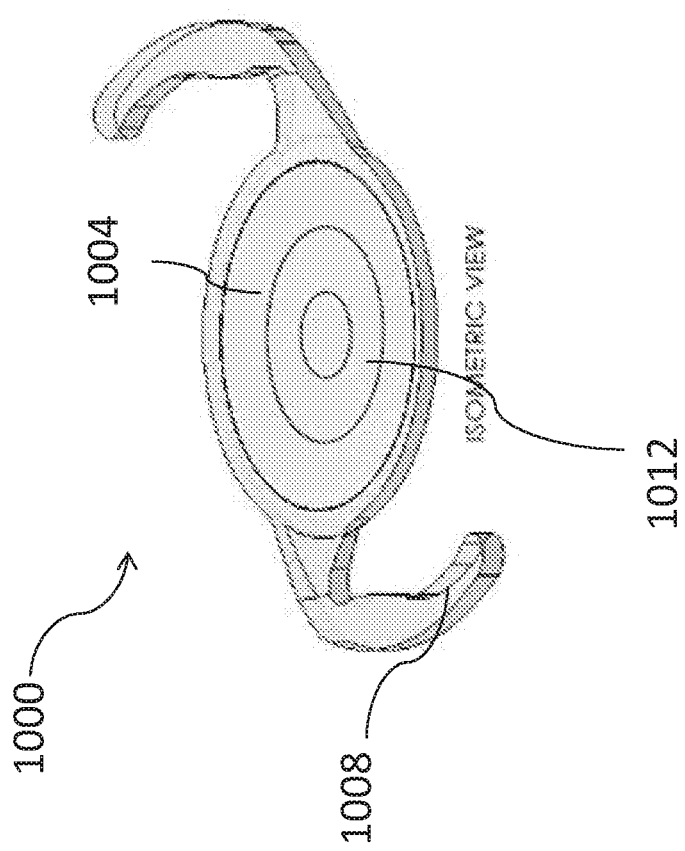
FIGURE 2D
FIGURE 2C

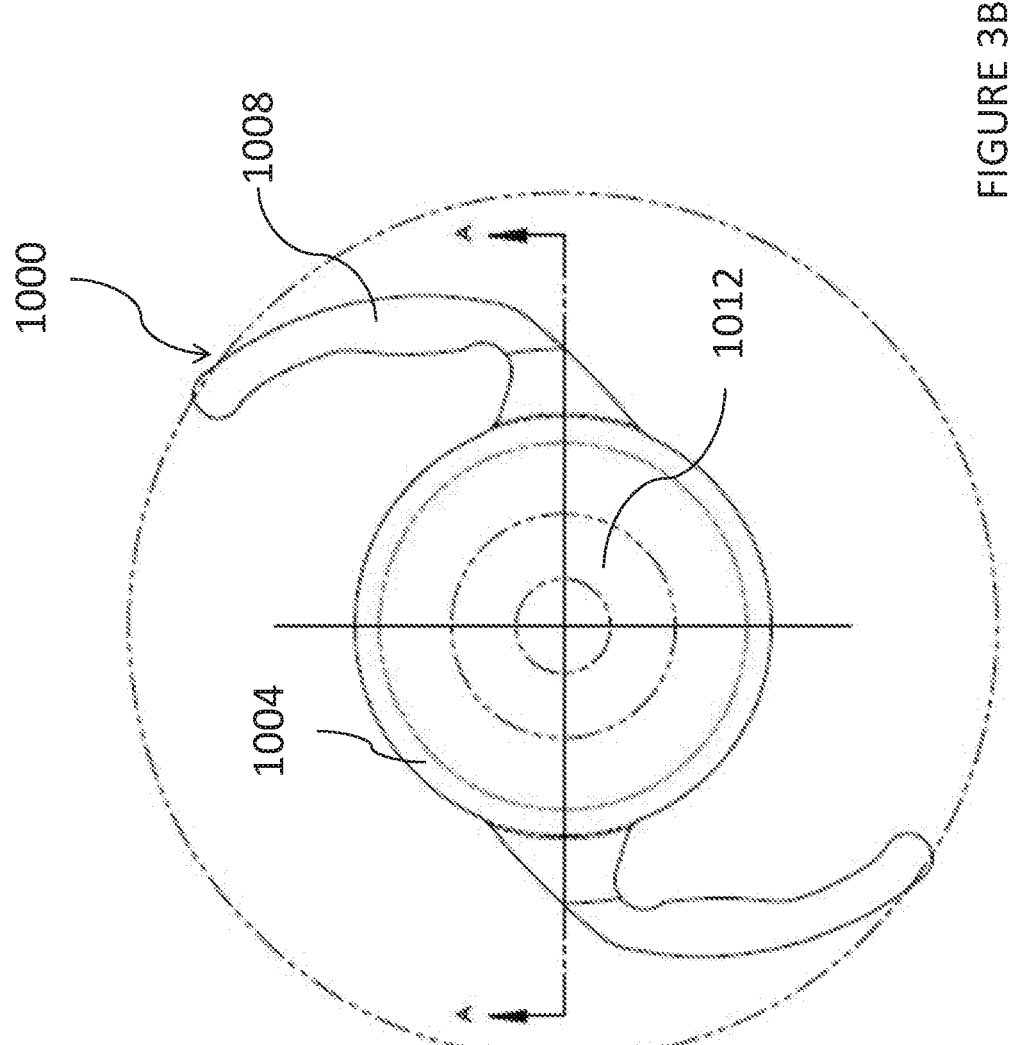
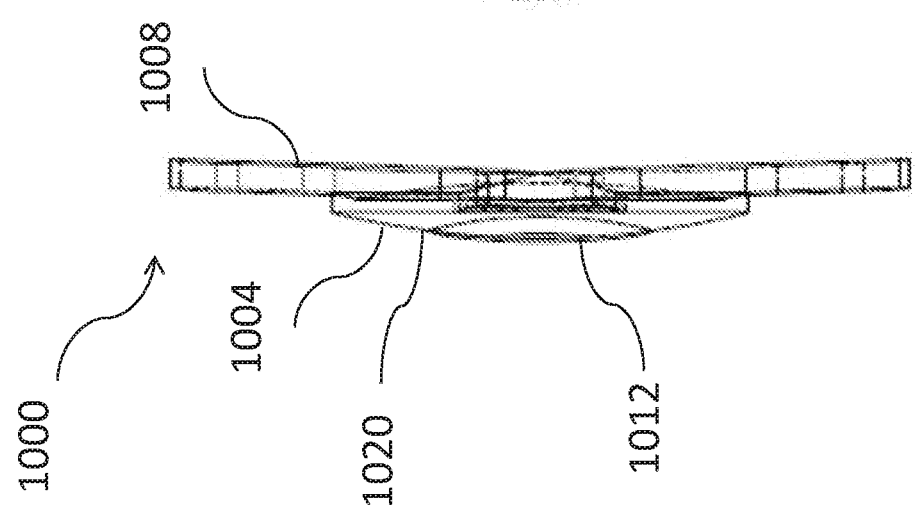
FIGURE 3B
FIGURE 3A

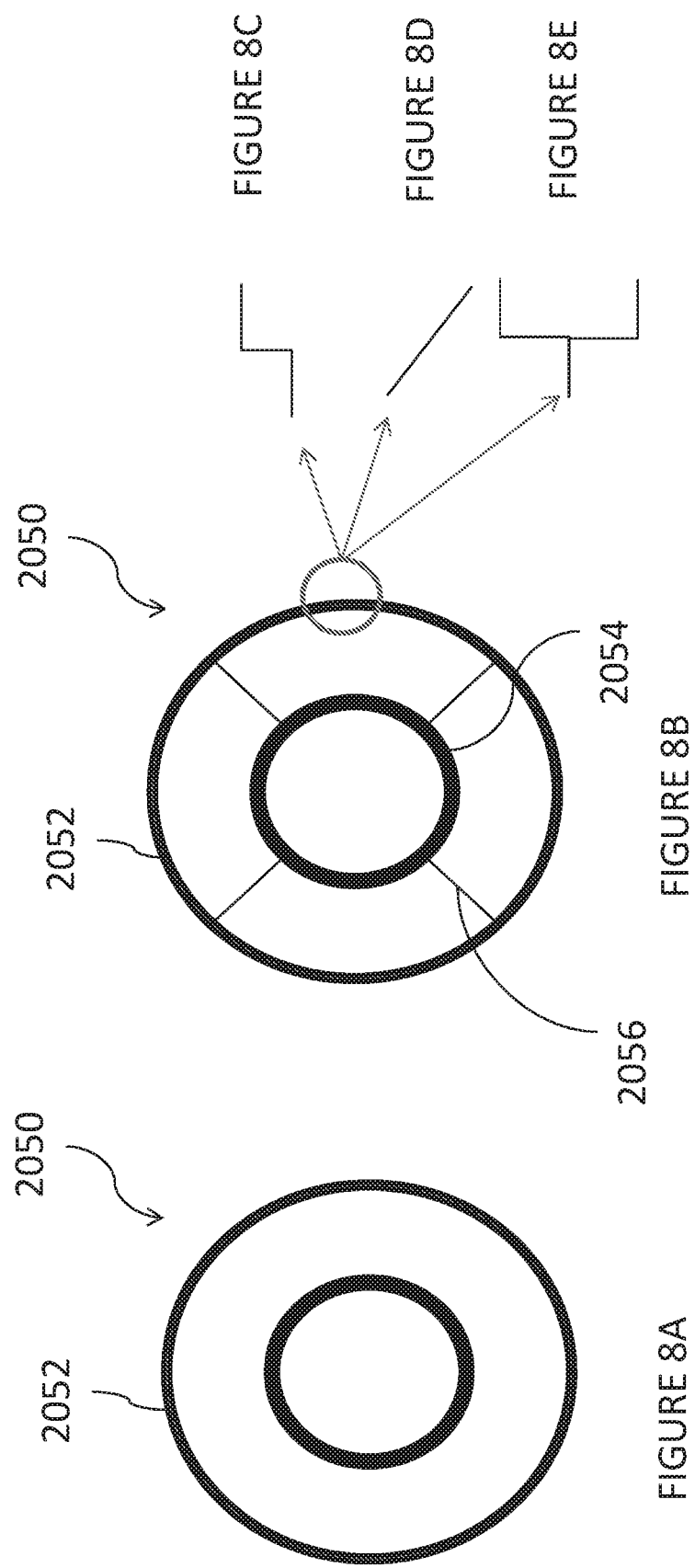

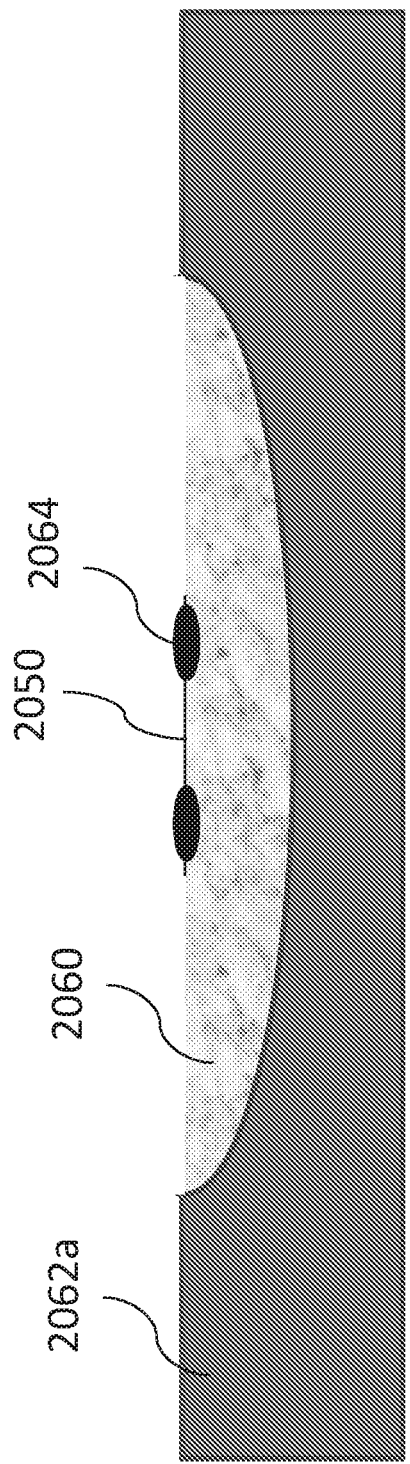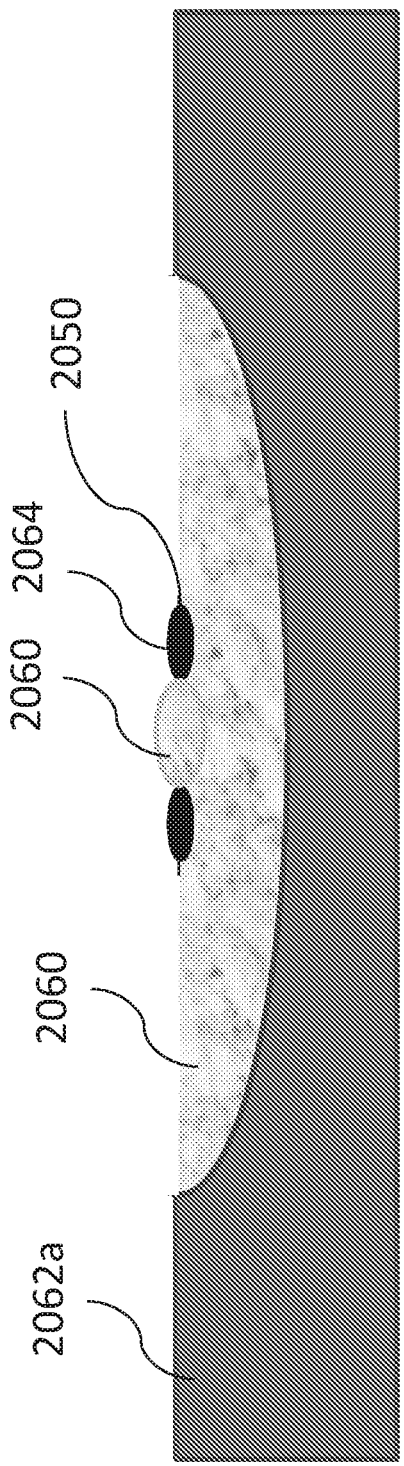

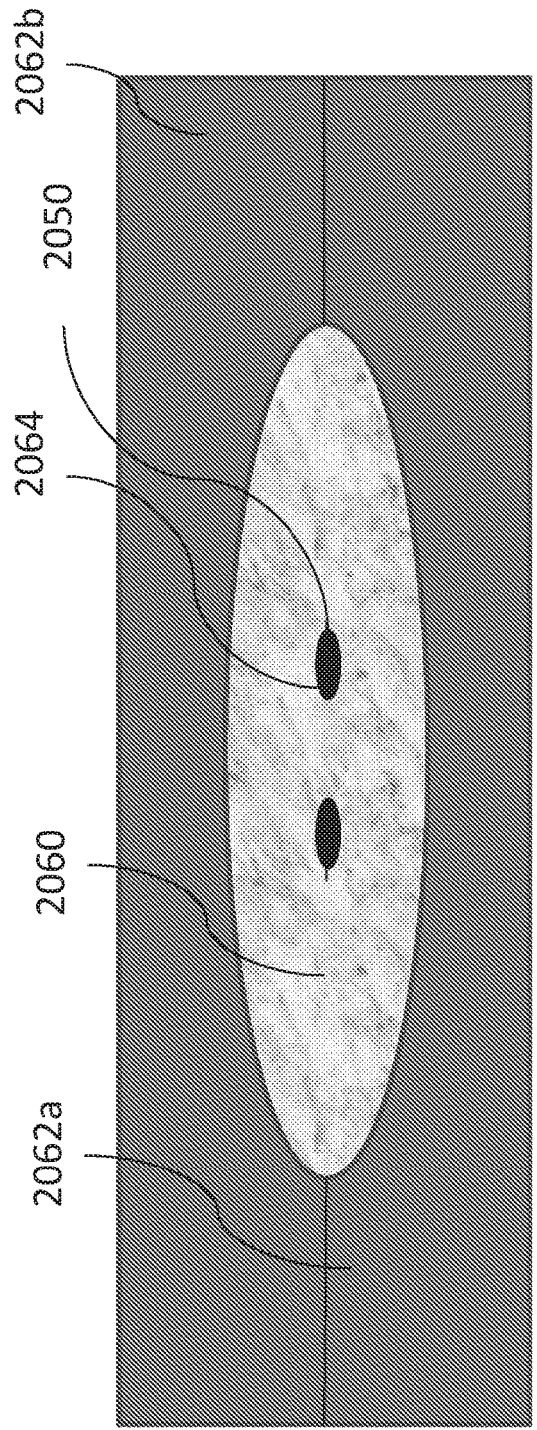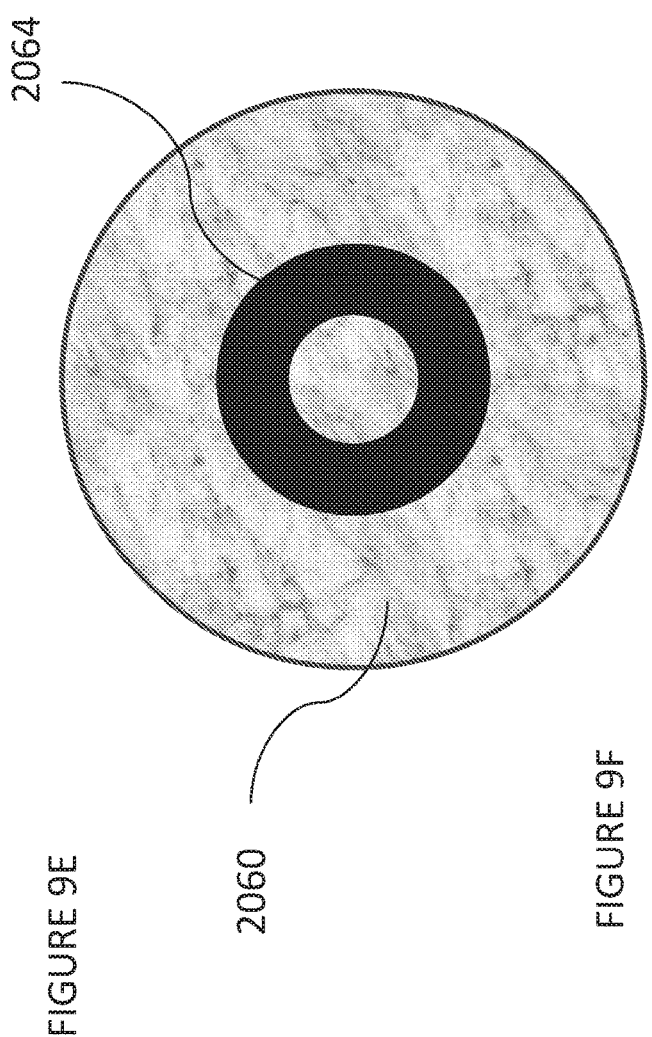
FIGURE 9E
FIGURE 9F

METHODS OF MOLDING INTRAOCULAR LENSES

RELATED APPLICATIONS

This application is a national stage application based on International Application No. PCT/US2016/055207, filed Oct. 3, 2016, which claims priority benefit of U.S. Patent Application No. 62/237,429, filed Oct. 5, 2015, which is hereby incorporated by reference in its entirety herein.

BACKGROUND

Field

This application relates generally to the field of intraocular devices. More particularly, this application is directed to intraocular implants and lenses (IOLs) with an aperture to increase depth of focus (e.g., "masked" intraocular lenses), and methods of making the same.

Description of the Related Art

The human eye functions to provide vision by transmitting and focusing light through a clear outer portion called the cornea, and further refining the focus of the image onto a retina by way of a crystalline lens. The quality of the focused image depends on many factors including the size and shape of the eye, and the transparency of the cornea and the lens.

The optical power of the eye is determined by the optical power of the cornea and the crystalline lens. In a normal, healthy eye, sharp images of distant objects are formed on the retina (emmetropia). In many eyes, images of distant objects are either formed in front of the retina because the eye is abnormally long or the cornea is abnormally steep (myopia), or formed in back of the retina because the eye is abnormally short or the cornea is abnormally flat (hyperopia). The cornea also may be asymmetric or toric, resulting in an uncompensated cylindrical refractive error referred to as corneal astigmatism.

Some people suffer from cataracts in which the crystalline lens undergoes a loss of transparency. In such cases, the crystalline lens can be removed and replaced with an intraocular lens (IOL). However, some intraocular lenses may still leave defects in a patient's non-distance eyesight.

SUMMARY

Methods of manufacturing masked intraocular lenses can include a molding process. In general, the molding process can include pouring an uncured material into a mold and then curing the material with a combination of UV light and heat temperature cycles. However, when performing a molding process with both optically transmissive and opaque materials (e.g., an optically transmissive optic material and an opaque mask material), it can be difficult to produce precise border lines between the optic and the aperture, which can reduce the optical performance of the intraocular lens.

The present disclosure is generally related to methods of manufacturing a masked intraocular lens with an annular mask embedded within or positioned on an anterior or a posterior surface of the optic. The mask and the optic may comprise the same material, such as an acrylic copolymer or silicone. The methods disclosed herein produce a precise border line at the interface between inner and outer diameters of the mask and the optic.

The method of manufacturing the intraocular lens can include filling an annular mask-forming feature (e.g., a trough) with an opaque mask material, adding optically transmissive optic material over the opaque mask material; and fully curing the opaque mask material and the optically transmissive optic material to form a mask and an optic. The mask can be sufficiently thick to prevent transmission of at least 90% of incident visible light (or at least about 98% of incident visible light). The annular mask-forming feature can be provided in a lens mold or in a partially-formed optic.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIGS. 2A-2D illustrate an embodiment of an intraocular lens having a mask positioned on an anterior surface of the optic.

FIGS. 3A-3D illustrate another embodiment of an intraocular lens having a mask positioned on a posterior surface of the optic.

FIGS. 8A-8E illustrate different embodiments of a mold delineator.

FIGS. 9A-9F illustrate a method of manufacturing an intraocular lens using the steps shown in FIG. 7.

DETAILED DESCRIPTION

Patients who undergo intraocular lens (IOL) implantation surgery may still suffer from defects in their non-distance eyesight (e.g., presbyopia). One technique for treating such defects is by including an annular mask within or on the optic that increases the patient's depth of focus. The light rays that pass through the aperture in the mask converge at a focal point on the retina, while the light rays that would not converge at the focal point on the retina are blocked by an opaque portion of the mask configured to prevent at least some or substantially all visible light from being transmitted through the mask.

Mask

Figure 1B:
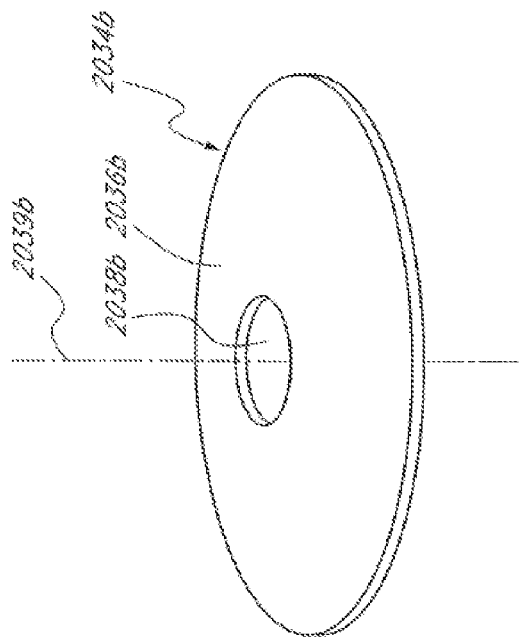
FIG. 1B illustrates another embodiment of the mask.
Figure 1A:
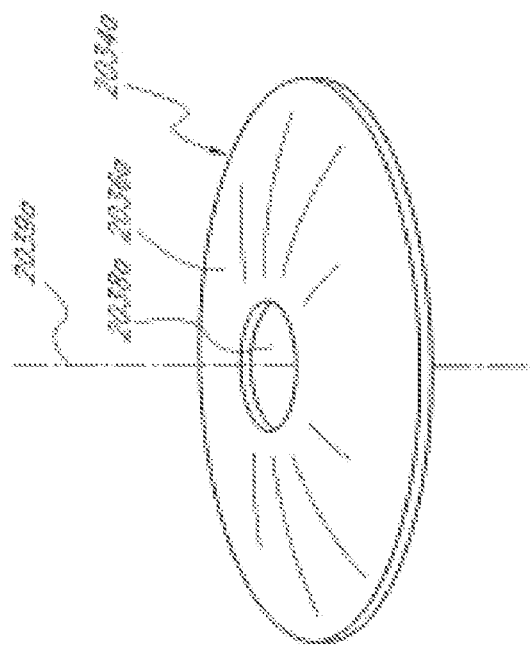
FIG. 1A illustrates an embodiment of a mask.
Figure 3D:
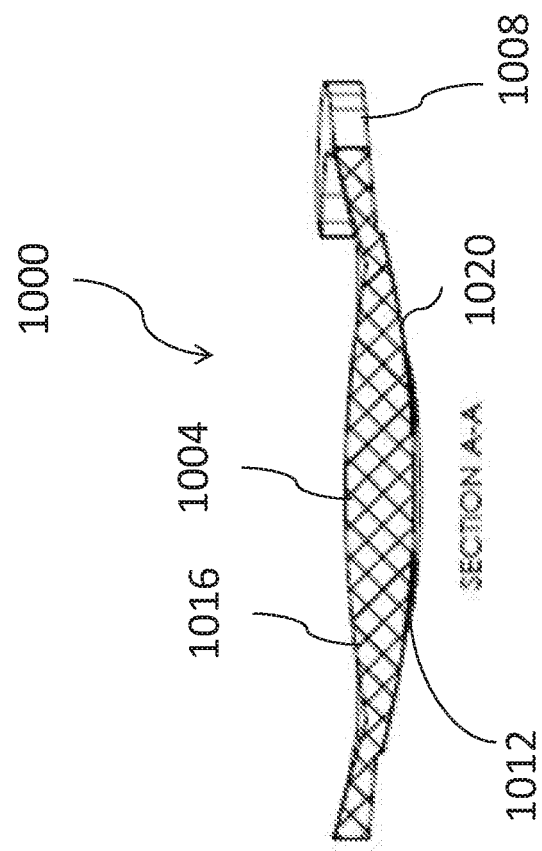
Figure 3C:
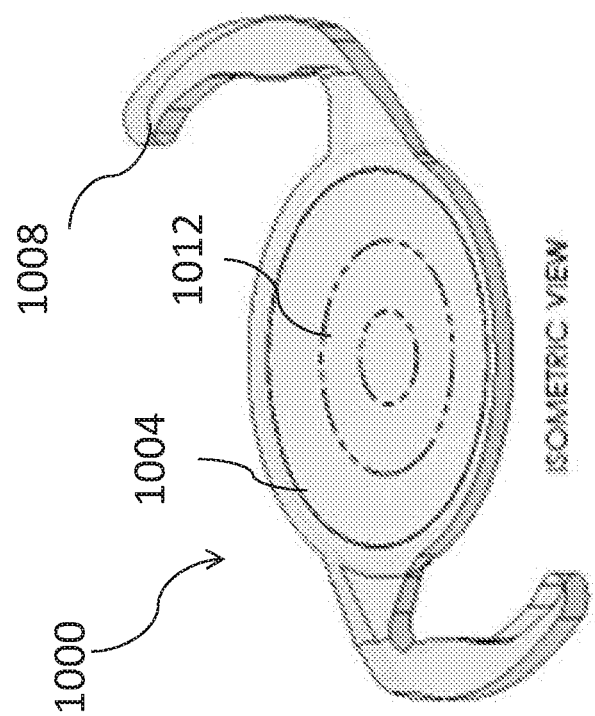
Figures 4A, 4B:
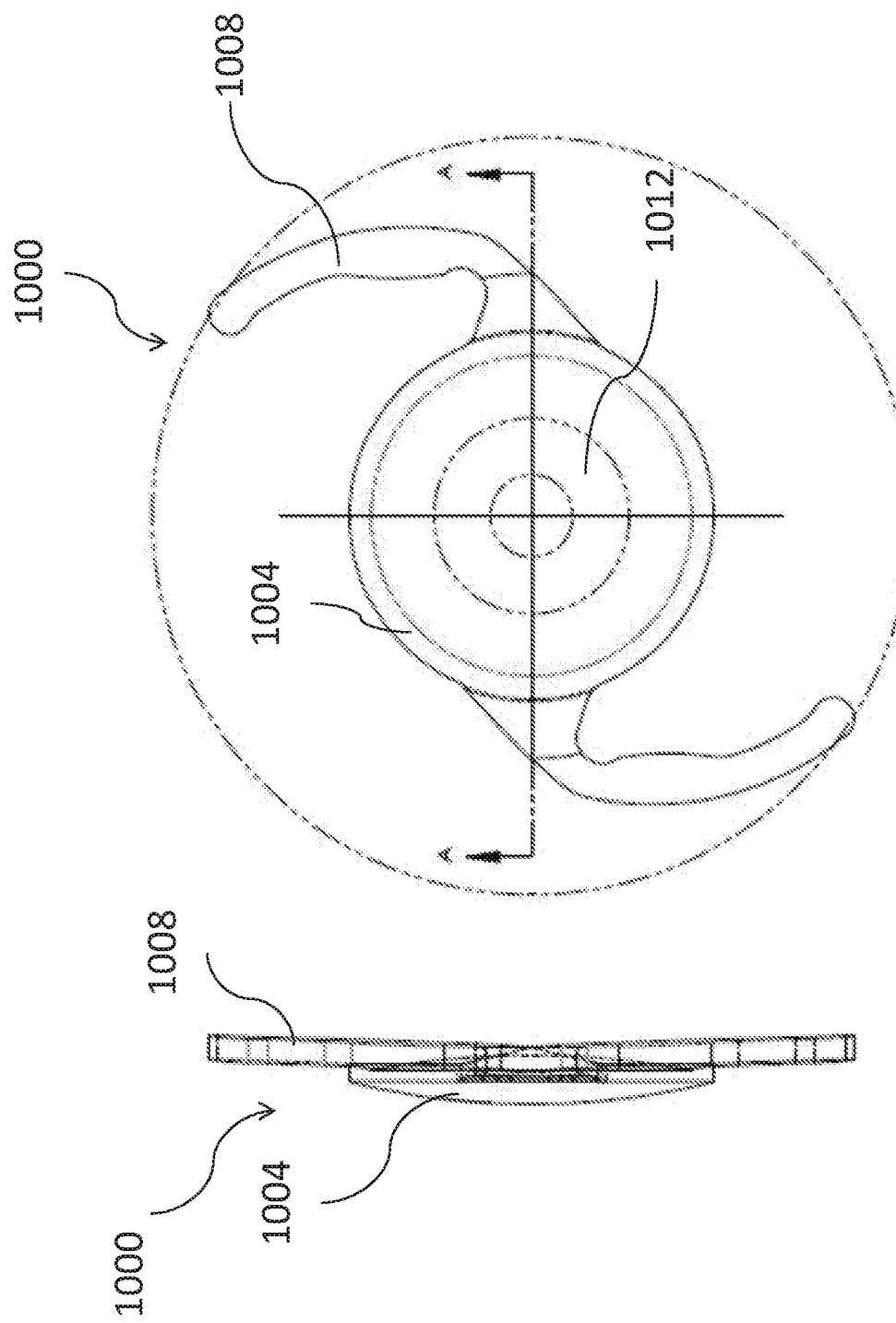
FIGS. 4A-4D illustrate yet another embodiment of an intraocular lens having a mask embedded in the optic.
Figures 4C, 4D:
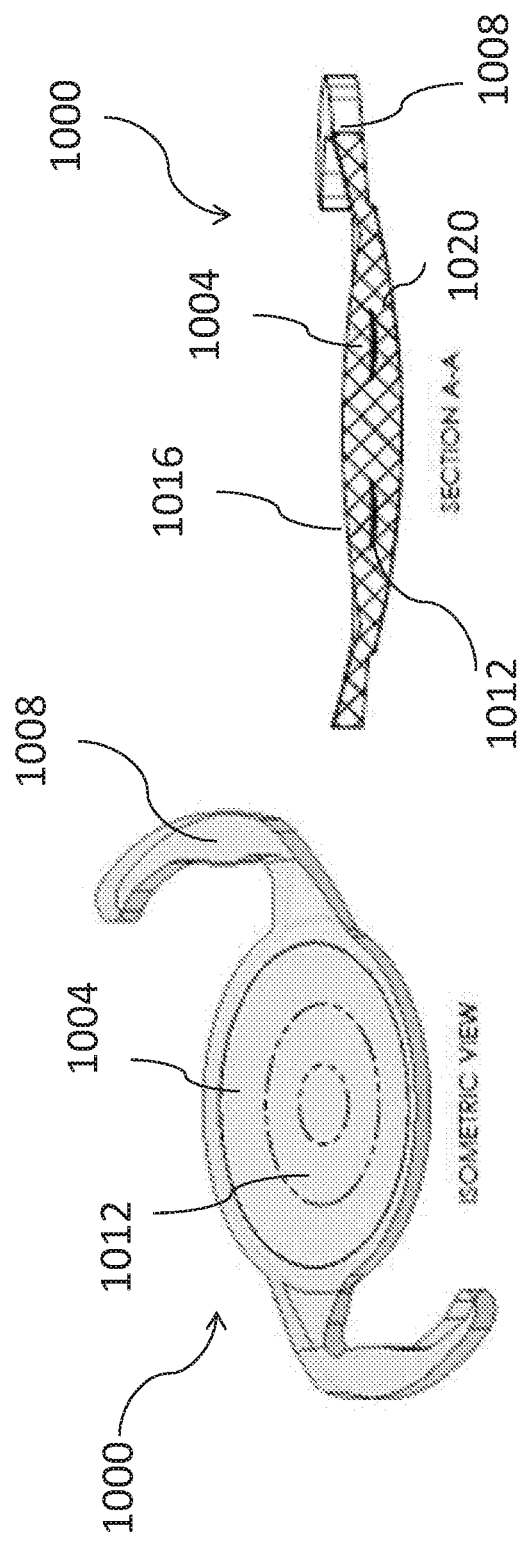

FIG. 1A illustrates a mask 2034a having an annular region 2036a surrounding an aperture 2038a substantially centrally located on the mask 2034a. An anterior surface of the annular region 2036a can have a curvature from the outer periphery to the inner periphery of the annular region 2036a, and the posterior surface of the annular region 2036a can have a similar curvature. However, as shown in FIG. 1B, the mask 2034b can also be flat. The mask 2034b can include an annular region 2034b surrounding an aperture 2038b substantially centered on the optical axis 2039b of the mask 2034b. Although the features described below are described with respect to the mask 2034a, one or the more of the features may be applied to the mask 2034b.

In some embodiments, the outer periphery of the mask 2034a is generally circular with an outer diameter of at least about 3 mm and less than about 6 mm. In some embodiments, the diameter of the outer periphery of the mask 2034a is at least about 3 mm and less than or equal to about 4 mm.

A thickness of the mask 2034a can be constant or can vary between the inner periphery (near the aperture) and the outer periphery. For example, the thickness may increase from an outer periphery and/or inner periphery of the mask 2034a and toward a radial midline of the annular region 2036a. In general, the thickness at any location of the mask 2034a can be less than or equal to about 200 microns, or less than or equal to about 100 microns, but preferably between about 1 micron and about 20 microns. For example, the thickness of the mask 2034a can be within the range: from about 1 micron to about 40 microns, from about 5 microns to about 20 microns, from about 5 microns to about 15 microns. In some implementations, the thickness of the mask 2034a can be within about two microns of: about 15 microns, about 10 microns, about 8 microns, or about 5 microns.

The aperture 2038a can transmit substantially all incident visible light along the optical axis 2039a. For example, the aperture 2038a can be a through-hole in the annular region 2036a or a substantially light transmissive (e.g., transparent to visible light) portion thereof. The aperture 2038a can be substantially circular and/or substantially centered around the optical axis 2039a of the mask 2034a. The size of the aperture 2038a can be any size that is effective to increase the depth of focus of an eye of a patient with presbyopia. In particular, the size of the aperture 2038a can be dependent on the location of the mask within the eye (e.g., distance from the retina). In some implementations, the aperture 2038a can have a diameter of at least about 0.85 mm and less than or equal to about 2.2 mm, at least about 1.1 mm and less than or equal to about 1.6 mm, or at least about 1.3 mm and less than or equal to about 1.4 mm.

The annular region 2036a can prevent transmission of substantially all or at least a portion of the spectrum of the incident visible light (e.g., radiant energy in the electromagnetic spectrum that is visible to the human eye) and/or the spectrum of non-visible light (e.g., radiant energy outside the range visible to humans). Preventing transmission of visible light through the annular region 2036a can block light that would not converge at the retina and fovea to form a sharp image. In some implementations, the annular region 2036a can prevent transmission of at least about: 90 percent of incident visible light, 92 percent of incident visible light, 95 percent of incident visible light, 98 percent of all incident visible light, or 99 percent of all incident visible light. In other words, the annular region 2036a can transmit no more than about: 10 percent of incident visible light, 8 percent of incident visible light, 5 percent of incident visible light, 3 percent of incident visible light, 2 percent of incident visible light, or 1 percent of incident visible light.

In some embodiments, opacity of the annular region 2036a is achieved because the material used to make mask 2034a is naturally opaque. In other embodiments, the material used to make the mask 2034a may be naturally substantially clear but treated with a dye or other pigmentation agent (e.g., carbon black).

Further variations of masks can be found in U.S. Pat. No. 7,628,810, filed May 26, 2004, U.S. Publication No. 2012/0143325, filed Feb. 19, 2012, U.S. Publication No. 2011/0040376, filed Aug. 13, 2010; U.S. Publication No. 2013/0268071, filed Nov. 30, 2012; U.S. Publication No. 2014/0264981; U.S. Publication No. 2015/0073549, filed Aug. 7, 2014; U.S. Pat. No. 5,662,706, filed Jun. 14, 1996; U.S. Pat. No. 5,905,561, filed Jun. 14, 1996; and U.S. Pat. No. 5,965,330, filed Dec. 6, 1996, all of which are included in the Appendix.

Intraocular Lens

As shown in FIGS. 2A-2D, the intraocular lens 1000 includes an optic 1004 and a mask 1012. The optic 1004 can be formed from an optically transmissive material, while the mask can be formed from an opaque material.

The optic 1004 may be monofocal or multifocal and it can have positive or negative optical power. The optic 1004 may be aspheric or any other configuration as the context may dictate. In some implementations, the greatest thickness of the optic 1004 is at the center of the optic 1004. In other implementations, the optic 1004 may have a reduced thickness at its center, which is further described in U.S. Publication No. 2011/0040376, filed Aug. 13, 2010, and is included in the Appendix. The optic 1004 may be substantially circular with an outer diameter between about 5.0 mm and about 8.0 mm, such as about 6.0 mm. A central thickness of the optic 1004 can be less than or equal to about 1.0 mm, such as between about 0.75 mm and about 1.0 mm.

The intraocular lens 1000 may include one or more haptics 1008 (e.g., one, two, three, four, or more) to prevent the intraocular lens 1000 from moving or rotating within the eye. As used herein the term "haptic" is intended to be a broad term encompassing struts and other mechanical structures that can be apposed against an inner surface of an eye and mounted to an optic to securely position an intraocular lens in an optical path of an eye. The haptics 1008 can be a variety of shapes and sizes depending on the location the intraocular lens 1000 is implanted in the eye. The haptics 1008 may be C-shaped, J-shaped, plate design, or any other design. The haptics 1008 may be manufactured substantially flat or vaulted with respect to the optic. Variations on the shape of the optic and the haptics can be found in U.S. Publication No. 2011/0040376, filed Aug. 13, 2010, which is included in the Appendix.

The mask 1012 can be formed on an anterior surface 1016 of the optic 1004 (see FIGS. 2A-2D), on a posterior surface 1020 of the optic 1004 (see FIGS. 3A-3D), or embedded within the optic 1004 (see FIGS. 4A-4D). When the mask 1012 is embedded within the optic 1004, the mask 1012 can be formed substantially at the midway line between the posterior 1020 and anterior surfaces 1016 of the optic 1004. But the mask 1012 can also be formed at other locations within the optic 1004.

Methods of Manufacturing

In some embodiments, the optic 1004 can be formed by molding a liquid lens material, such as an acrylic or silicone material, and curing the material into a solid. A completed solid mask 1012 can be pre-manufactured (e.g., from a different material than the optic) and positioned on or in the optic as part of this molding process. However, in this type of process where the mask 1012 is pre-manufactured and then molded into the optic, there is a potential for an inadequate bond between the mask and the optic. In addition, if the mask and the optic are made of different materials, there is a potential that the optical performance of the intraocular lens can be compromised due to the mask and optic materials potentially having elasticities and/or thermal expansion properties, which are too dissimilar. For example, if the material properties of the optic 1004 and the mask 1012 are not adequately compatible, then deformations, such as those resulting from injection forces during surgical implantation or swelling that may occur during manufacture due to chemical extractions, may damage the intraocular lens. Similarly, temperature shifts that occur during manufacture and/or surgical implantation can also damage the intraocular lens.

It can therefore be advantageous to manufacture the intraocular lens using a process where the mask is molded from the same material as the optic (e.g., a liquid acrylic or silicone material) at the same general time and/or such that the mask and optic undergo similar curing sequences (e.g., the mask and optic can be at least partially cured together). For example, the mask can be formed from a liquid material that has been modified to be substantially opaque by mixing in a dark pigment dye or dark particles, whereas the optic can be formed from the unmodified transparent liquid material. In this type of manufacturing process, however, mixing, bleeding, and/or blending can occur between the opaque mask material and the transparent optic material. If this occurs, the outer and inner diameter borders of the mask can become blurred and/or diffuse. This can negatively impact the optical performance of the intraocular lens.

This mixing, bleeding, and/or blending of the opaque and transparent liquid materials can be reduced or prevented by providing a mask-forming feature in the lens mold which can help prevent the opaque material from spreading beyond the desired region where the mask is to be formed on the surface of the optic or within the optic. In some embodiments, the mask-forming feature can be an annular trough formed in the lens mold at the location where the mask is to be positioned. This mask-forming trough can have inner and outer diameters, which correspond to the desired size of the mask. The opaque material used to form the mask can be added to fill this trough. Transparent material used to form the optic can be added over or around the opaque material in the mask-forming trough. The trough can help to prevent the opaque material from mixing, bleeding, and/or blending with the transparent material in a way that would blur the outer or inner diameter of the mask. The trough can achieve this, for example, through surface tension, which helps to hold the opaque material in place. In this way, more precise mask borders can be achieved. For example, the inner border line of the mask (which defines the central circular aperture 2038) and the outer border line of the mask (which defines the outer circular perimeter of the mask 2034) can each be circular to within ±100 microns (e.g., any location along the inner or outer border of the mask can be within 100 microns of a perfect circle [or within 75 microns, or within 50 microns, or within 25 microns]). In addition, the outer border and the inner border can be concentric to within ±200 microns (e.g., the outer border and the inner border at any given angular position can be within 200 microns of being perfectly concentric [or within 150 microns, or within 100 microns, or within 50 microns]).

When forming an intraocular lens with the mask positioned on an anterior or posterior surface of the optic, a lens forming surface of the lens mold can include a mask-forming feature located at a position where the mask is to be formed. The mask-forming feature can be generally annular and defined by an outer edge and an inner edge. These edges can be sharp knife edges in order to more effectively hold the opaque mask material in place via surface tension. The lens forming surface can also include an optic region positioned radially inward and/or outward of the mask-forming feature. As just mentioned, the mask-forming feature can be an annular trough. This trough can be etched, machined, or otherwise cut into the lens forming surface of the lens mold. The trough can have a minimum depth that creates a mask thickness which provides less than 5% light transmission (or less than 3% or less than 2%). In some embodiments, the depth of the trough can be at least about 4 microns, or between about 5 microns and about 10 microns. But the trough can be as deep as practically appropriate without causing dissimilar material property interactions between the mask material and the optic material, resulting in poor injection performance (e.g., a maximum trough depth of about 150 microns).

The optic region of the lens forming surface of the mold will generally be curved in order to provide the intraocular lens with refractive optical power. In such embodiments, the mask-forming feature can have a different radius of curvature than the optic region. This difference in radius of curvature can result in a trough in the lens forming surface to create the mask-forming feature and facilitate the creation of a precise border between the mask and the optic. The radius of curvature of the mask-forming feature can be between about 25% and about 50% of the radius of the optic region, such as between about 25% and 35%, between about 30% and about 40%, between about 35% and about 45%, between about 40% and about 50%, or otherwise. In some implementations, the radius of curvature of the mask-forming feature can be between about 30% and about 35% of the radius of the optic region, such as about 32%. In other embodiments, however, the mask-forming feature and the optic region can have the same radius of curvature, but can be separated by a stepped transition.

Figure 5:
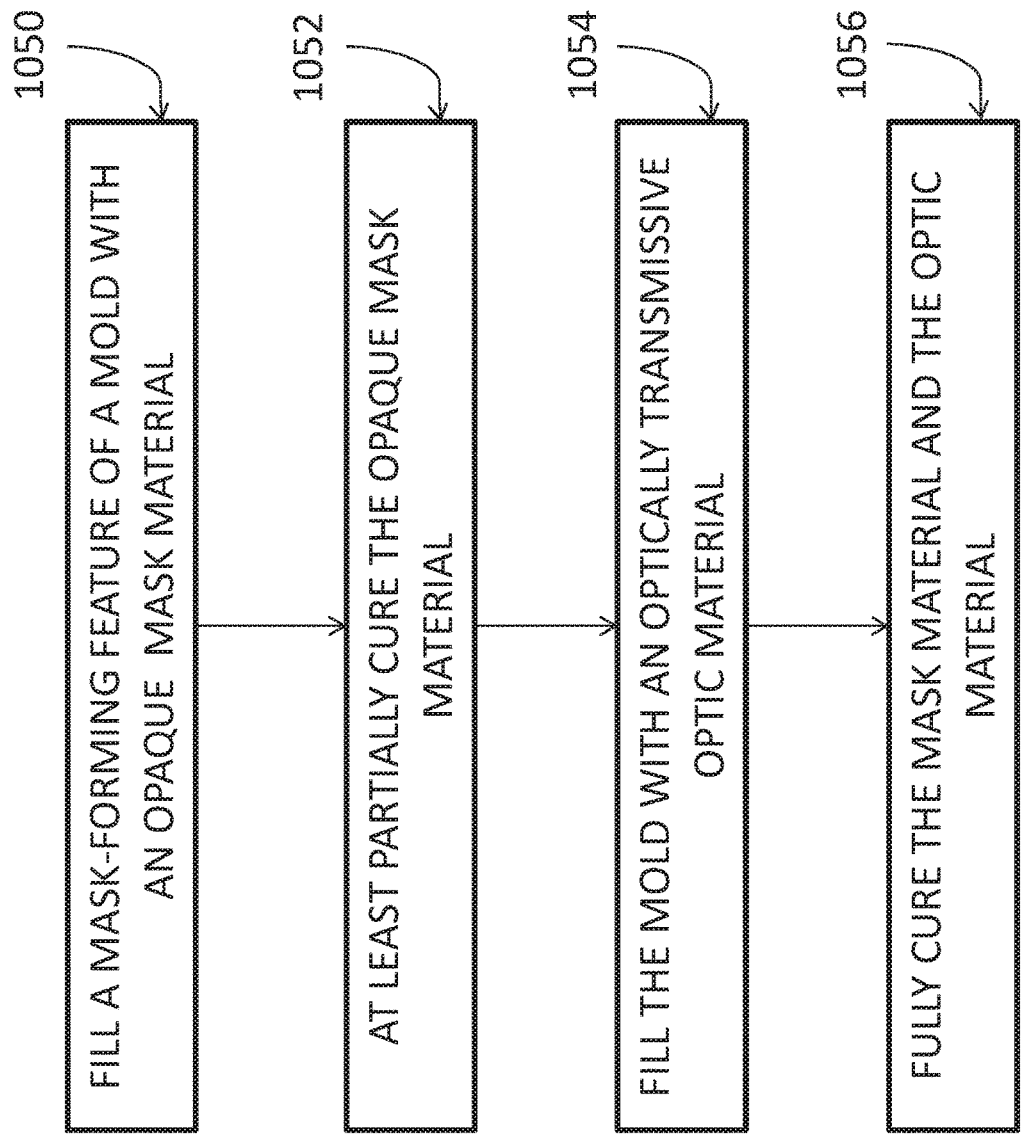
FIG. 5 is a flow chart of a method of manufacturing an intraocular lens with a mask positioned on a surface of the optic.
Figure 6:
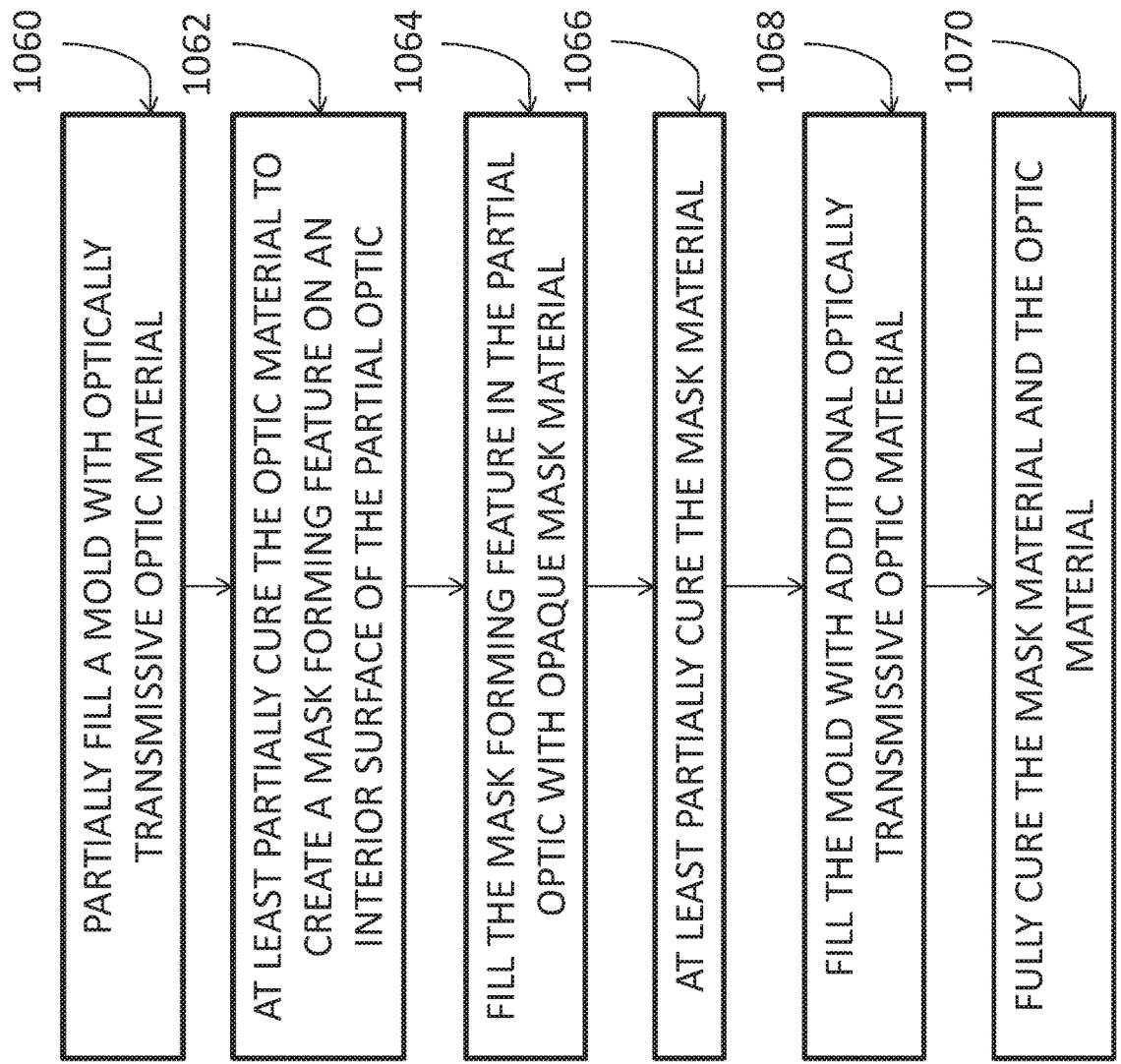
FIG. 6 is a flow chart of a method of manufacturing an intraocular lens with a mask embedded in the optic.
Figure 7:
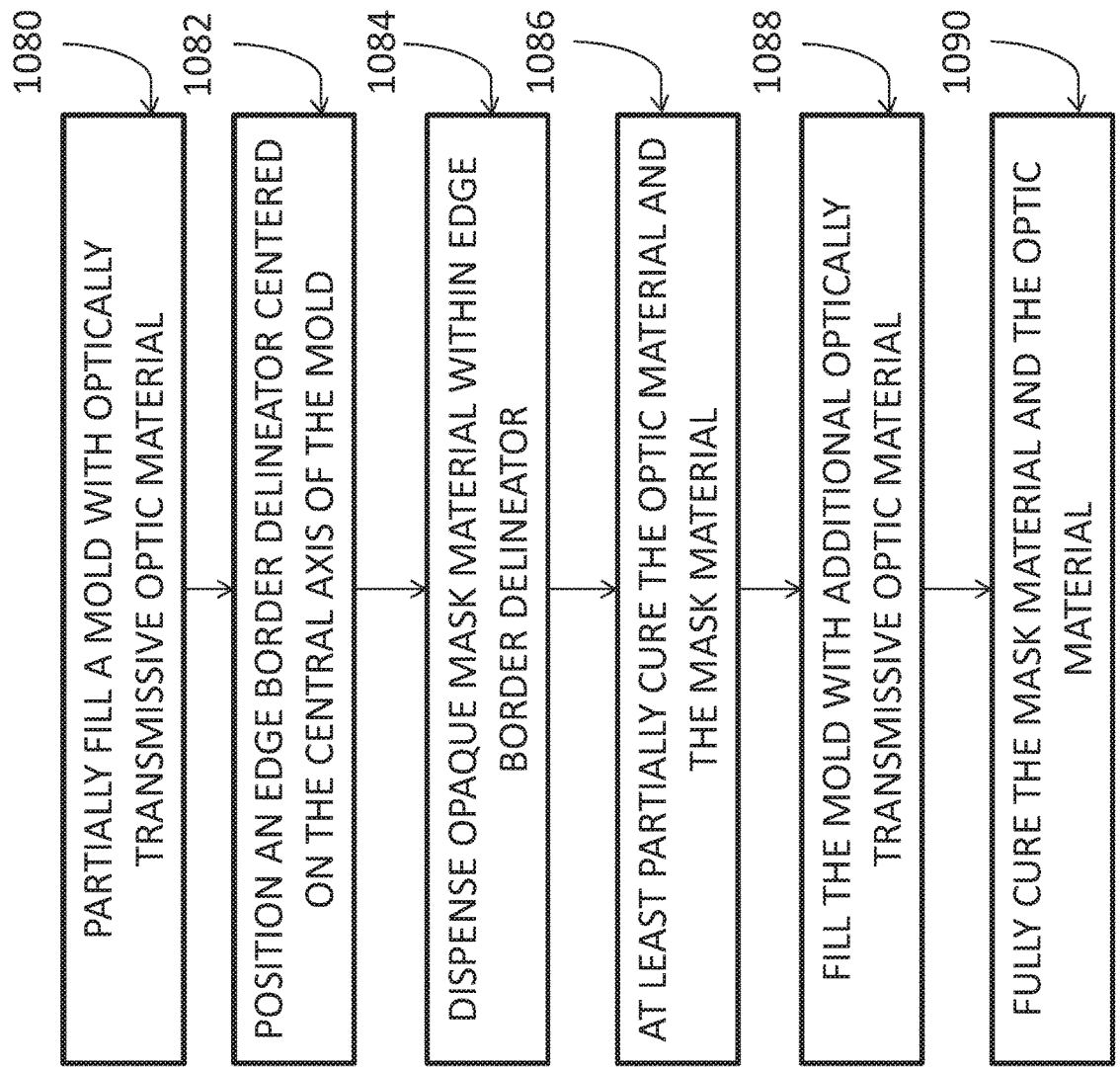
FIG. 7 is a flow chart of another method of manufacturing an intraocular lens within a mask embedded in the optic.

FIG. 5 is a flow chart illustrating a method of manufacturing an intraocular lens with a mask positioned on the anterior or posterior side of the optic. The method can include preparing a mixture of uncured mask material (e.g., an acrylic copolymer or silicone) mixed or impregnated with a high density of carbon black particles or other black dye or pigments as needed to provide opaque properties (e.g., to permit no more than about 2% light transmission). A specific and precise volume of uncured opaque mask material can be dispensed (e.g., with a cannula) to fill the mask-forming feature and define an outer diameter and an inner diameter of the mask (block 1050). By relying on surface tension and capillary action of the viscous mask material, the dispensed volume can be specifically controlled to conform to the outer and inner edges of the mask-forming feature of the mold. The exposed surface of the uncured mask material (i.e., opposite the lens forming surface) can exhibit a curvature. To achieve these results, the mask material can have a viscosity and/or surface tension that can range from approximately that of water to acetic acid per as specified below:

| Fluid | Absolute Viscosity | | | Surface Tension |
|---|---|---|---|---|
| | (N s/m$^2$, Pa s) | (cp) | (10$^4$ lb$_m$/ft sec) | mN/m |
| Acetic acid | 0.0011550 | 1.155 | 7.760 | 27.60 @ 20 C. |
| Water | 0.0008900 | 0.890 | 6.000 | 71.95 @ 25 C. |

After filling the mask-forming feature, the mask can optionally be partially or fully cured using, for example, a combination of UV light and heat cycles (block 1052). Thereafter, the mold can be filled with an optically transmissive optic material, which may be the same as the mask material (e.g., acrylic or silicone), to over-mold the mask (block 1054). Finally, the mask material and the optic material can be fully cured—again, using a combination of UV light and heat cycles (block 1056).

In an alternative embodiment, the intraocular lens may be manufactured with the mask embedded within the optic. The method can include at least partially filling a first mold portion with an uncured optic material (block 1060). The first mold portion can be filled up to the depth where the mask is to be formed in the interior of the optic. In this way, the optic is initially only partially formed just to the thickness where the mask will be embedded in the completed optic. In this case, the first mold portion need not include a mask-forming feature. Instead, a second mold portion, which mates with the first mold portion, can include a structure that is the physical complement of the desired mask-forming feature. For example, the second mold portion can include an annular projection located where the mask is to be formed. The annular projection will form a trough in the partially-formed optic. As discussed further below, after at least partial curing of the optic material in the first mold portion, this trough in the partially-formed optic becomes the mask-forming feature and can be filled with opaque mask material.

After the first and second mold portions are mated together, the uncured transparent optic material can be partially or fully cured to form a trough in the interior surface of the partial optic (block 1062). The trough in the partial optic can be filled with an opaque mask material (block 1064). The opaque mask material can be prepared, for example, by mixing or impregnating an optically transmissive mask material (e.g., an acrylic copolymer or silicone) with a high density of carbon black particles or other black dye or pigments as needed to provide opaque properties (e.g., to permit no more than about 2% light transmission). A specific and precise volume of uncured opaque mask material can be dispensed (e.g., with a cannula) to exactly fill the trough in the partial optic and define an outer diameter and an inner diameter of the annular mask. By relying on surface tension and capillary action of the viscous mask material, the dispensed volume can be specifically controlled to conform to the outer and inner edges of the trough in the partial optic. The exposed surface of the uncured mask material (i.e., opposite interior surface of the optic) can exhibit a curvature. After filling the trough in the partial optic, the mask can optionally be partially or fully cured (block 1066). Thereafter, the mold can be filled with additional optic material to over-mold the mask (block 1068). A third mold portion can be used in place of the second mold portion to form an outer surface of the optic. Finally, the mask material and the optic material can be fully cured (block 1070). In some implementations, one of the mold portions may include a protruding pin that defines the inner diameter of the mask-forming feature and radially centers the mask in the optic.

Figure 9A:
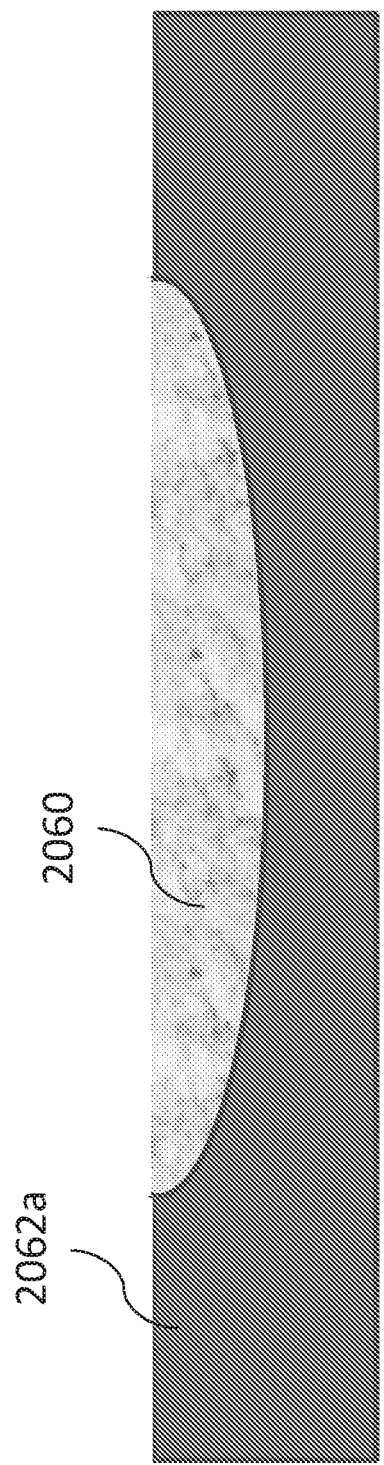
Figure 9B:
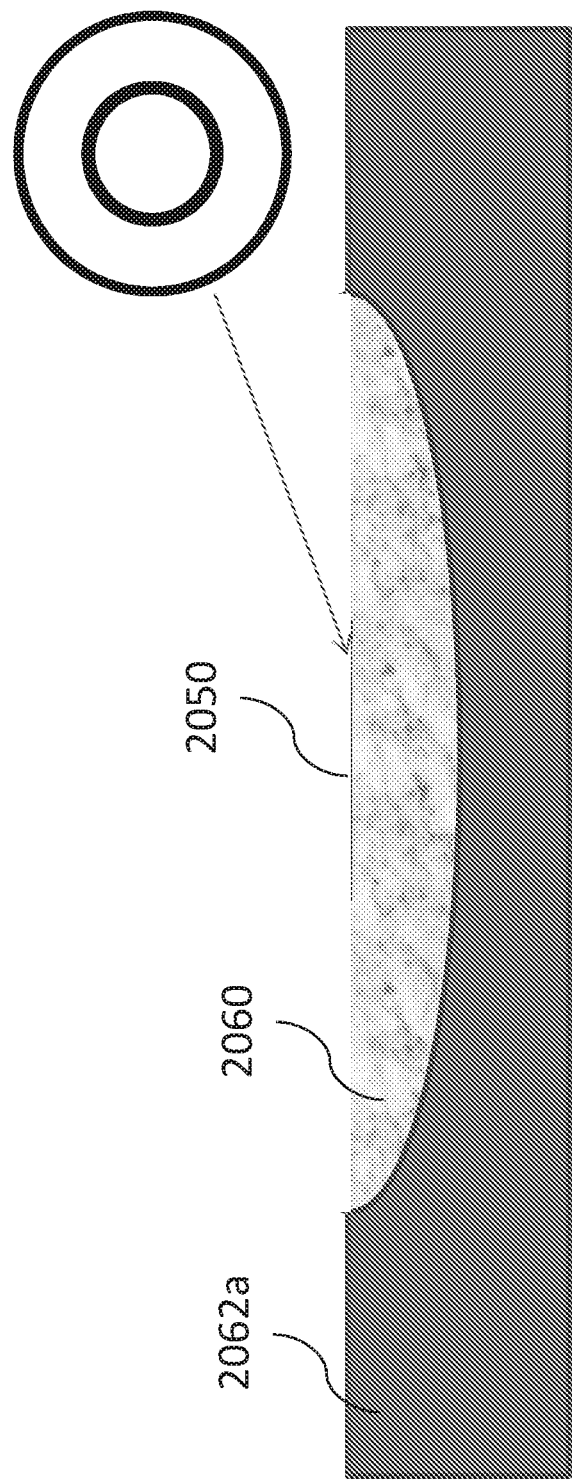

An alternative method of manufacturing an intraocular lens with an embedded mask is illustrated in FIG. 7 and FIGS. 9A-9F. A measured partial volume of liquid type uncured optic material 2060 can be placed in a mold half 2062*a* (block 1080 and FIG. 9A). An edge border delineator 2050 can be placed on the center of the liquid optic material 2060 (block 1082 and FIG. 9B). A bead of opaque mask material 2064 can be dispensed within the lines of the edge border delineator 2050 (block 1084). The opaque mask material 2064 wicks to the confinements of the edge border delineator 2050 (FIG. 9C). Optionally, a bead of uncured optic material 2060 can be dispensed within the central aperture of the edge border delineator 2050 (FIG. 9D). The bead of optic material 2060 wicks to the inner periphery of the edge border delineator. At least the surface of the optic material 2060 can be partially cured at this time (block 1086). A measured partial volume of uncured optic material 2060 can be placed into the opposite mold half 2062*b* (block 1088). The two mold halves 2062*a*, 2062*b* can then be joined together and the intraocular lens can be put through the full curing process (block 1090 and FIG. 9E). Thereafter, the intraocular lens can be removed from the mold (FIG. 9F).

FIG. 8A illustrates an embodiment of the edge border delineator 2050. The edge border delineator 2050 can include an outer border 2052 spaced apart from an inner border 2054. As explained above, the opaque mask material can be dispensed between the outer border 2052 and the inner border 2054. The bead of optic material can be dispensed radially inward of the inner border 2054. The edge border delineator 2050 can be made from compatible polymer or elastic type polymer material (e.g., an acrylic copolymer or silicone). A width of the inner and/or outer border 2054, 2052 (e.g., in a radial direction) can be within a range of 100 microns to 500 microns. The thickness of the inner and/or outer border 2054, 2052 (e.g., in an anterior-posterior direction) can be between about 5 and 15 microns thick with a flat formed shape. Connecting spokes 2056 may or may not be used to maintain inner and outer border concentricity (see FIG. 8B). The cross-sectional profile of the inner and/or outer border 2054, 2052 can be vertical, stair stepped (see FIG. 8C), sloped (see FIG. 8D), fully contained (see FIG. 8E), or any other profile to facilitate the wicking/capillary action of the liquid acrylic as necessary. A plurality of mechanical locking holes can be provided in the edge border delineator to support capillary action and to minimize delamination of the intraocular during injection.

Terminology

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately" "about," and "substantially" as used herein represent an amount close to the stated amount that still performs a desired function or achieves a desired result. For example, the terms "approximately,"

"about," and "substantially" may refer to an amount that is within less than 10% of the stated amount, as the context may dictate.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 3 mm" includes "3 mm."

Although certain embodiments and examples have been described herein, it will be understood by those skilled in the art that many aspects of the methods and IOLs shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A method of manufacturing an intraocular lens, the method comprising:
    filling an annular mask-forming feature in a lens mold with an opaque mask material, the annular mask-forming feature comprising a trough provided in a portion of the lens mold;
    adding optically transmissive optic material over the opaque mask material; and
    fully curing the opaque mask material and the optically transmissive optic material to form a mask and an optic, the mask being sufficient to prevent transmission of at least 90% of incident visible light.

2. The method of claim 1, further comprising preparing the opaque mask material by mixing an optically transmissive material with an opaque agent.

3. The method of claim 2, wherein the optically transmissive material comprises acrylic.

4. The method of claim 2, wherein the opaque agent comprises carbon black.

5. The method of claim 1, further comprising at least partially curing the opaque mask material before adding the optically transmissive optic material over the opaque mask material.

6. The method of claim 5, wherein at least partially curing the opaque mask material comprises fully curing the opaque mask material.

7. The method of claim 1, wherein the mask is sufficient to prevent transmission of at least about 98% of incident visible light.

8. The method of claim 1, wherein the opaque mask material and the optically transmissive optic material comprise the same material.

9. The method of claim 8, wherein the same material comprises acrylic.

10. The method of claim 1 wherein a surface of the annular mask-forming feature has a radius of curvature that is about 25% to about 50% of a radius of curvature of the optic.

11. The method of claim 10, wherein the radius of curvature of the surface of the annular mask-forming feature is between about 30% and about 35% of the radius of curvature of the optic.

12. The method of claim 1, wherein the optic is monofocal.

13. An intraocular lens formed by the method of claim 1.

14. A method of manufacturing an intraocular lens, the method comprising:
    adding optically transmissive optic material to a lens mold;
    providing a border delineator on the optically transmissive optic material in the lens mold;
    filling the border delineator with an opaque mask material; and
    fully curing the opaque mask material and the optically transmissive optic material to form a mask and an optic, the mask being sufficient to prevent transmission of at least 90% of incident visible light.

15. The method of claim 14, wherein filling the border delineator with the opaque mask material comprises dispensing the opaque mask material between inner and outer borders of the border delineator.

16. The method of claim 14, further comprising, after filling the border delineator with the opaque mask material, dispensing a bead of optically transmissive optic material within an aperture of the border delineator.

* * * * *